United States Patent [19]

Hu et al.

[11] Patent Number: 5,595,909
[45] Date of Patent: Jan. 21, 1997

[54] FILTER DEVICE

[75] Inventors: Wei-Shou Hu, Falcon Heights; Frank B. Cerra, Edina, both of Minn.

[73] Assignee: Regents of the University of Minnesota, Minneapolis, Minn.

[21] Appl. No.: 414,499

[22] Filed: Mar. 31, 1995

Related U.S. Application Data

[63] Continuation-in-part of Ser. No. 609,371, Oct. 29, 1990, abandoned, and Ser. No. 376,095, Jan. 20, 1995, which is a continuation of Ser. No. 864,893, Apr. 3, 1992, abandoned, which is a continuation-in-part of Ser. No. 355,115, May 18, 1989, abandoned, which is a continuation-in-part of Ser. No. 197,700, May 23, 1988, abandoned.

[51] Int. Cl.$^6$ .................................................. C12M 3/06
[52] U.S. Cl. ................ 435/297.4; 435/182; 435/240.22; 435/240.242; 435/299.1; 604/4
[58] Field of Search ........................... 435/1.1, 41, 70.3, 435/174, 176, 177, 180, 182, 240.1, 240.2, 240.22, 240.241, 240.242, 284.1, 297.1, 297.2, 297.4, 299.1, 299.2, 1.2; 210/321.64, 321.72, 321.78, 321.75, 321.8, 321.84, 321.87, 321.9; 604/4–6; 623/66

[56] References Cited

FOREIGN PATENT DOCUMENTS

89/11529  11/1989  WIPO .

OTHER PUBLICATIONS

Scholz et al. "A two-compartment cell entrapment bioreactor with three different holding times for cells, high and low molecular weight compounds." Cytotechnology, vol. 4 (1990), pp. 127–137. 1990.

Peshwa, M. V. et al., "Kinetics of hepatocyte spheroid formation", Biotechnol. Prog., 10, 460–466 (1994).

Lazar, A. et al., "Formation of porcine hepatocyte spheroids for use in a bioartificial liver", Cell Transplantation, 4, 259–268 (1995).

Lazar, A. et al., "Extended liver-specific functions of porcine hepatocyte spheroids entrapped in collagen gel", In Vitro Cell. Dev. Biol., 31, 340–346 (1995).

Wu, F. J. et al., "Entrapment of hepatocyte spheroids in a hollow fiber bioreactor as a potential bioartificial liver", Tissue Engineering, 1, 29–40 (1995).

Koide, N. et al., "Continued high albumin production by multicellular . . . ", Biochem. Biophys. Res. Comm., 161, 385–391 (1989).

Koide, N. et al., "Formation of multicellular spheroids composed of adult rat . . . ", Exp. Cell Res., 186, 227–235 (1990).

Tong, J. Z. et al., "Long-term culture of adult rat hepatocyte spheroids", Exp. Cell Res., 200, 326–332 (1992).

Li, A. P. et al., "Culturing of primary hepatocytes as entrapped aggregates . . . ", In Vitro Cell. Dev. Biol. 29A, 249–254 (1993).

Sakai, Y. et al., "A hollow fiber bioreactor immobilizing . . . ", Animal Cell Tech.: Basic & Applied Aspects, 6:417–421. Eds. T. Kobayshi et al. Kluwer Pub, Netherlands (1994).

Takabatake, H. et al., "Encapsulated multicellular spheroids of rat hepatocytes . . . ", Artif. Organs, 15 474–480 (1991).

Yagi, K. et al., "Rapid formation of multicellular spheroids of adult rat . . . ", Artif. Organs, 17, 929–934, (1993).

*Primary Examiner*—William Beisner
*Attorney, Agent, or Firm*—Sughrue, Mion, Zinn, Macpeak & Seas

[57] ABSTRACT

A filter device containing cell masses and single cells is described. The device contains porous hollow fibers and hepatocytes entrapped within a contracted gel matrix.

20 Claims, 8 Drawing Sheets

FILTER DEVICE

Portions of the research described herein were supported in part by grants from the National Institutes of Health.

This is a continuation-in-part of application Ser. No. 08/376,095 filed 20 Jan. 1995, which is a continuation of application Ser. No. 07/864,893 filed 3 Apr. 1992, abandoned, which is a continuation-in-part of application Ser. No. 07/355,115 filed 18 May 1989, abandoned, which is a continuation-in-part of application Ser. No. 07/197,700 filed 23 May 1988, abandoned and of application Ser. No. 07/605,371 filed 29 Oct. 1990, abandoned. Those applications are incorporated by reference herein in entirety.

BACKGROUND OF THE INVENTION

Liver transplantation currently is the only mode of treatment for patients in acute fulminant hepatic failure who are not responding to supportive therapy (Starzl et al. "Liver Transplantation (1)" *N Engl J Med* (1989) 321:1092–1099; Langer and Vacanti "Tissue Engineering" *Science* (1993) 260:920–926). The need for an interim liver assist device as a bridge to transplantation for patients in hepatic failure has been well documented (Takahashi et al. "Artificial Liver: State of the Art" *Dig Diseases Sci* (1991) 36:1327–1340). With the development of an artificial liver, patients in hepatic failure may be supported until donor livers become available or until their own livers can regenerate. Such a device would alleviate the problem of scarcity of donor organs (Busuttil et al. "The First 100 Liver Transplants at UCLA" *Ann Surg* (1987) 206:387–402; Vacanti et al. "Liver Transplantation in Children: The Boston Center Experience in the First 30 Months" *Transplant Proc* (1987) 19:3261–3266.) and associated complications (Walvatne & Cerra "Hepatic Dysfunction in Multiple Organ Failure" In *Multiple Organ Failure: Pathophysiology and Basic Concepts of Therapy*, Dietch, E. A., Ed., (1990) pp. 241–260, Thieme Medical Publishers, New York; Shellman et al. "Prognosis of Patients with Cirrhosis and Chronic Liver Disease Admitted to the Medical Intensive Care Unit" *Crit Care Med* (1988) 16:671–678).

Animal cells and genetically altered derivatives thereof often are cultivated in bioreactors for the continuous production of vaccines, monoclonal antibodies and pharmaceutic proteins, such as hormones, antigens, tissue type plasminogen activators and the like. The cells essentially are a system of catalysts and the medium supplies and removes the nutrients and growth inhibiting metabolites. To supply nutrients and remove metabolites, the medium in the bioreactor is changed either intermittently or continuously by fluid flow. However, because of relatively small size and small density difference when compared to the medium, cells inevitably are withdrawn when the medium is changed, resulting in a relatively low cell concentration within the bioreactor. As a result of the low cell concentration, the concentration of the desired cell product is low in the harvested medium.

An ideal animal cell bioreactor would include three features:
(1) cells would be retained in a viable state at high densities in the bioreactor apparatus as long as possible, with an almost infinite residence time;
(2) high molecular weight compounds, including expensive growth factors and the desired cell products, would have a long but finite residence time within the bioreactor to allow for both efficient nutrient utilization by the growing cells and also the accumulation of cell products to a high concentration; and
(3) low molecular weight compounds, including less expensive nutrients and inhibitory substances, should have a very short residence time within the bioreactor to reduce inhibition of cell growth, cell product formation and other cellular metabolic activities.

The development of an artificial liver is a complex problem. Many prior attempts, such as plasmapheresis, charcoal and resin hemoperfusion and xenograft cross circulation, have failed. Unlike the heart that has one major physiologic function, the liver performs many complex tasks necessary for survival. Those tasks have been difficult to develop or maintain in mechanical systems.

The liver is the metabolic factory required for the biotransformation of both endogenous and exogenous waste molecules and the synthesis of glucose, lipids and proteins, including albumin, enzymes, clotting factors and carrier molecules for trace elements. The liver maintains appropriate plasma concentrations of amino and fatty acids as well as detoxifying nitrogenous wastes, drugs and other chemicals. Waste products, such as bilirubin, are conjugated and excreted via the biliary tree. Hepatic protein synthesis and biotransformation vastly increase the complexity of hepatic support.

Systems that employ hepatocytes to provide biochemical function are problematic because hepatocytes can be difficult to maintain in culture. Under standard conditions, non-transformed hepatocytes cultured on plastic lose gap junctions in about 12 to 24 hours; flatten, become agranular, lose all tissue specific functions in 3–5 days; and die within 1–2 weeks. (Reid & Jefferson "Culturing hepatocytes and other differentiated cells" *Hepatology* (1984) May-June; 4(3): 548–59; Warren et al. "Influence of medium composition on 7-alkoxycoumarin O-dealkylase activities of rat hepatocytes in primary maintenance culture" *Zenobiotica* (1988) 18(8):973–81).

A solution to that problem is the use of transformed hepatocytes which can be grown much more easily. However, transformed hepatocytes often are considered a poor choice because even well-differentiated transformed cells show marked variations in tissue-specific function from the parent tissues. (Reid & Jefferson (1984) supra) Moreover, many cell lines are transformed by viruses. (Aden et al. "Controlled synthesis of HBsAg in a differentiated human liver carcinoma-derived cell line" *Nature* (1979) pp. 615–6; Knowles et al. "Human hepatocellular carcinoma cell lines secrete the major plasma proteins and hepatitis B surface antigen" *Science* (1980) 209:497–9). Those cell lines have the potential to transmit the transforming virus to the patient. As a result, it is doubtful that regulatory agencies would approve the use of transformed cells for humans, even if the risk of transmission were proven minimal.

Many approaches to prolonging the viability and function of cultured hepatocytes and other differentiated cells have been investigated. Those approaches include adding hormones and growth factors to the culture media, adding extracellular matrix constituents and growing the hepatocytes in the presence of another cell type. Cells routinely used in co-culture work with hepatocytes are endothelial cells or hepatic nonparenchymal cells, such as Kupffer cells.

The addition of corticosteroids to the incubation media has been shown to prolong survival of cultured hepatocytes and to maintain albumin synthesis, particularly in synergy with insulin. (Jefferson et al. "Post-transcriptional modulation of gene expression in cultured rat hepatocytes" *Mol Cell Biol* (1984) 4(9):1929–34; Dich et al. "Long-term culture of hepatocytes: effect of hormones on enzyme activities and metabolic capacity" *Hepatology* (1988) 8(1):39–45) DMSO (Dimethyl sulfoxide) and phenobarbital also are known to prolong hepatocyte viability and function. (Maher, J. J. "Primary hepatocyte culture: is it home away from home?" *Hepatology* (1988) 8(5):1162–6) Not all tissue-specific functions are supported equally, however. Insulin can promote some functions with an effect that varies with concentration. If only insulin is added to the medium, urea cycle enzyme expression is decreased. That negative effect can be counteracted by the addition of glucagon and dexamethasone. (Dich et al. (1988) supra)

Hormonally-defined medium also can prolong hepatocyte function and viability. (Jefferson et al. (1984) supra) Using a serum-free hormonally-defined medium, good function in baboon hepatocytes has been shown for over 70 days. The medium consisted of epidermal growth factor (100 ng/ml), insulin (10 μg/ml), glucagon (4 mg/ml), albumin (0.5 mg/ml), linoleic acid (5 mg/ml), hydrocortisone ($10^{-6}$ M), selenium ($10^{-7}$ M), cholera toxin (2 ng/ml), glycyl-histidyl-lysine (20 ng/ml), transferrin (5 mg/ml), ethanolamine prolactin ($10^{-6}$ M), (100 ng/ml), somatotropin (1 mg/ml) and thyrotropin releasing factor ($10^{-6}$ M). (Lanford et al. "Analysis of plasma protein and lipoprotein synthesis in long-term primary cultures of baboon hepatocytes maintained in serum-free medium" *In Vitro Cell Dev Biol* (1989) 25(2):174–82)

It now is clear that the extracellular matrix has considerable influence on cell function and survival. (Bissell & Aggeler "Dynamic reciprocity: How do extracellular matrix and hormones direct gene expression" *Mechanisms of Signal Transduction by Hormones and Growth Factors* Alan R. Liss, Inc. (1987) 251–62.3) Matrix elements have been shown to reduce or obviate the need for specific growth factors. Using extracted hepatic connective tissue, hepatocytes have been cultured for over 5 months and maintained albumin synthesis for at least 100 days. That extract represented approximately 1% of the liver by weight. One-third of the extract was composed of carbohydrates and noncollagenous proteins; the other two-thirds were collagens, 43% Type I, 43% Type III, and the remainder, an undefined mixture of others including Type IV. (Rojkind et al. "Connective tissue Biomatrix: Its Isolation and Utilization for Long-term Cultures of Normal Rat Hepatocytes" *J Cell Biol* (1980) 87:255–63) That mixture may not reflect accurately the local hepatocyte environment, the peri-sinusoidal space or Space of Disse.

The presence of matrix in the Space of Disse has been controversial. Some researchers initially suggested that the peri-sinusoidal space was "empty". It now is appreciated that all of the major constituents of basement membrane are present in or around the Space of Disse. (Bissell & Choun "The role of extracellular matrix in normal liver" *Scand J Gastroenterol* (1988) 23(Suppl 151):1–7)

Heparan sulfate proteoglycan binds both cell growth factors and cells. (Saksela et al. "Endothelial cell-derived heparan sulfate binds basic fibroblast growth factor and protects it from proteolytic degradation" *J Cell Biol* (1988) 107(2):743–51; Gordon et al. "Heparan sulfate is necessary for adhesive interactions between human early hemopoietic progenitor cells and the extracellular matrix of the marrow microenvironment" *Leukemia* (1988) 2(12):804–9) Heparan sulfate may effect directly the hepatocyte nucleus. (Ishihara et al. "Transport of heparan sulfate into the nuclei of hepatocytes" *J Biol Chem* (1986) 261(29):13575–80), Hepatocytes secrete relatively abundant quantities of heparan sulfate in culture. (Arenson et al. "Formation of extracellular matrix in normal rat liver: lipocytes as a major source of proteoglycan" *Gastroenterology* (1988) 95(2):441–7) Immunologic studies identified Type I collagen, Type III collagen, Type IV collagen, fibronectin and laminin in the Space of Disse. (Geerts et al. "Immunogold localization of procollagen III, fibronectin and heparan sulfate proteoglycan on ultrathin frozen sections of the normal rat liver". *Histochemistry* (1986) 84(4–6):355–62; Martinez-Hernandez, A. "The hepatic extracellular matrix. I. Electron immunohistochemical studies in normal rat liver" *Lab Invest* (1984) 51(1):57–74) There normally is little Type I collagen in the Space of Disse, although hepatocytes in culture show increasing Type I synthesis with de-differentiation, at the expense of Type III collagen synthesis. That effect is reversed with culture techniques that support tissue-specific hepatocyte activity.

Hepatocytes also can be cultured on Matrigel™, a biomatrix produced by a sarcoma cell line (EHS). Matrigel™ contains Type IV collagen, laminin, entactin and heparan sulfate. On Matrigel™, hepatocytes maintain normal albumin synthesis for 21 days. (Bissell & Aggeler (1987) supra).

Close duplication of the normal environment of the hepatocyte also has been attempted by culturing hepatocytes in a confluent monolayer on collagen. A second layer of Type I collagen is added to recreate the normal matrix "sandwich" formed on the "top" and on the "bottom" of the hepatocyte. That technique has shown significantly improved viability and function with albumin synthesis for more than 42 days. (Dunn et al. "Hepatocyte function and extracellular matrix geometry: long-term culture in a sandwich configuration" *FASEB* (1989) 3:174–7)

The effect of various proteoglycans and glycosaminoglycans on gap junction protein synthesis and genetic expression also has been examined carefully. The most effective compounds were dermatan sulfate proteoglycan, chondroitin sulfate proteoglycan, and heparan. Heparan extracted from the liver was most effective. Lambda carrageenan, a seaweed extract, also was effective. (Spray et al. "Proteoglycans and Glycosaminoglycans Induce Gap Junction Synthesis and Function in Primary Liver Cultures" *J Cell Biol* (1987) 105:541–55) Finally, chitosan, a polysaccharide found in crustacean shells and fungal membranes, has been suggested as a factor that can mimic normal matrix and promote function and survival of cells. (Muzzarelli et al. "Biological activity of chitosan: ultrastructural study" *Biomaterials* (1988) 9(3):247–52; Scholz & Hu "A two compartment cell entrapment bioreactor with three different holding times for cells, high and low molecular weight compounds" *Cytotechnology* (1990) 4:127–137).

Another successful technique for culturing differentiated liver cells involves co-culture with nonparenchymal cells. Recently, co-culture of hepatocytes on various endothelial lines was compared. Co-culture showed significantly improved albumin synthesis and maintenance of gap junctions. The cells were grown in the presence of insulin and dexamethasone. The addition of serum did not improve the results. The improved survival and function conferred by co-culture occurred only with cells in close proximity and was not transferred by cell supernatants. (Goulet et al. "Cellular interactions promote tissue-specific function, biomatrix deposition and junctional communication of primary cultured hepatocytes" *Hepatology* (1988) 8(5):1010–8).

It still is controversial whether the beneficial effects of co-culture occur through matrix interactions or require cell-cell contact.

There also is evidence that lipocytes play a key role in matrix production. Lipocytes are reported to be as numerous as Kupffer cells and have been suggested to produce the majority of Type I collagen, Type II collagen, Type IV collagen, laminin and proteoglycans, particularly dermatan sulfate proteoglycan and chondroitin sulfate proteoglycan. (Friedman et al. "Hepatic lipocytes: The principle collagen-producing cells of normal rat liver" *PNAS* (1985) 82:8681–5) It is of particular interest that those specific proteoglycans were those that best support gap junctions (Spray et al. (1987) supra).

Many techniques of artificial support have been utilized over the past three and a half decades. Those include simple exchange transfusions (Lee & Tink "Exchange transfusion in hepatic coma: report of a case" The *Med J Australia* (1958) 11:40–42; Trey et al. "Treatment of hepatic coma by exchange blood transfusion" *NEJM* (1966) 274(9):473–81); plasmapheresis with plasma exchange (Sabin & Merritt "Treatment of hepatic coma in cirrhosis by plasmapheresis and plasma infusion [plasma exchange]" *Annals of Internal Medicine* (1968) 68(1):1–6); extracorporeal heterologous or homologous liver perfusion (Eisemann et al. "Heterologous liver perfusion in treatment of hepatic failure" *Annals of Surgery* (1965) 162(3):329–345; Sen et al. "Use of isolated perfused cadaveric liver in the management of hepatic failure" *Surgery* (1966) 59(5):774–781); cross-circulation (Burnell et al. "Acute hepatic coma treated by cross-circulation or exchange transfusions" *NEJM* (1967) 276(17):943–953); hemodialysis (Opolon et al. "Hepatic failure coma (HFC) treated by polyacrylonitrile membrane (PAN) hemodialysis (HD)" *Trans ASAIO* (1976) 22:701–710); activated charcoal hemoperfusion (Gazzard et al. "Charcoal haemoperfusion in the treatment of fulminant hepatic failure" *Lancet* i:1301–1307); and, more recently, bioartificial liver systems (BAL's) containing cultured hepatocytes.

Examples of bioartificial liver systems currently being investigated for support of liver failure include extracorporeal bioreactors (Arnaout et al. "Development of bioartificial liver: bilirubin conjugation in Gunn rats" *Journal of Surgical Research* (1990) 48:379–382; Margulis et al. "Temporary organ substitution by hemoperfusion through suspense of active donor hepatocytes in a total complex of intensive therapy in patients with acute hepatic insufficiency" *Resuscitation* (1989) 18:85–94); implantable hepatocyte cultures, such as microencapsulated gel droplets (Cai et al. "Microencapsulated hepatocytes for bioartificial liver support" *Artificial Organs* (1988) 12(5):388–393) and spheroid aggregates (Saito et al. "Transplantation of spheroidal aggregate cultured hepatocytes into rat spleen" *Transplantation Proceedings* (1989) 21(1):2374–77).

Those bioartificial liver systems have the advantage of performing detoxification, synthesis and bioprocessing functions of the normal liver. Only a few extracorporeal bioreactors have been used in the clinical setting (Matsumura et al. "Hybrid bioartificial liver in hepatic failure: preliminary clinical report" *Surgery* (1987) 101(1):99–103; Margulis et al. (1989) supra). Implantable hepatocyte cultures remain clinically untested.

The technique for hepatocyte entrapment within microencapsulated gel droplets (hepatocyte microencapsulation) is similar to the technique successfully used for pancreatic islet encapsulation (O'Shea & Sun "Encapsulation of rat islets of Langerhans prolongs xenograft survival in diabetic mice" *Diabetes* (1986) 35:943–46; Cai et al. (1988) supra). Microencapsulation allows nutrient diffusion to the hepatocytes and metabolite and synthetic production diffusion from the hepatocytes. Microencapsulation also provides intraperitoneal hepatocytes with "immuno-isolation" from the host defenses (Wong & Chang "The viability and regeneration of artificial cell microencapsulated rat hepatocyte xenograft transplants in mice" *Biomat Art Cells Art Org* (1988) 16(4):731–739).

Plasma protein and albumin synthesis (Sun et al. "Microencapsulated hepatocytes as a bioartificial liver" *Trans ASAIO* (1986) 32:39–41; Cai et al. (1988) supra); cytochrome P450 activity and conjugation activity (Tompkins et al. "Enzymatic function of alginate immobilized rate hepatocytes" *Biotechnol Bioeng* (1988) 31:11–18); gluconeogenesis (Miura et al. "Liver functions in hepatocytes entrapped within calcium alginate" *Ann NY Acad Sci* (1988) 542:531–32); ureagenesis (Sun et al. "Microencapsulated hepatocytes: an in vitro and in vivo study" *Biomat Art Cells Art Org* (1987) 15:483–486); and hepatic stimulating substance production (Kashani & Chang "Release of hepatic stimulatory substance from cultures of free and microencapsulated hepatocytes: preliminary report" *Biomat Art Cells Art Org* (1988) 16(4):741–746) all have been reported for calcium alginate-entrapped hepatocytes.

Aggregated hepatocytes have been proposed as a treatment means for fulminant hepatic failure. Multiple techniques exist for hepatocyte aggregation (Saito et al. "Transplantation of spheroidal aggregate cultured hepatocytes into rat spleen" *Transplantation Proceedings* (1989) 21(1):2374–77; Koide et al. "Continued high albumin production by multicellular spheroids of adult rat hepatocytes formed in the presence of liver-derived proteoglycans" *Biochem Biophys Res Comm* (1989) 161(1):385–91).

Extracorporeal bioreactor designs for the purpose of artificial liver support have included perfusion of small liver cubes (Lie et al. "Successful treatment of hepatic coma by a new artificial liver device in the pig" *Res Exp Med* (1985) 185:483–494) dialysis against a hepatocyte suspension (Matsumura et al. (1987) supra; Margulis et al. (1989) supra); perfusion of multiple parallel plates (Uchino et al. "A hybrid bioartificial liver composed of multiplated hepatocyte monolayers" *Trans ASAIO* (1988) 34:972–977); and hollow fiber perfusion. Human studies using extracorporeal hepatocyte suspensions have been reported.

The first clinical report of artificial liver support by dialysis against a hepatocyte suspension was released in 1987 (Matsumura et al. (1987) supra). The device consisted of a rabbit hepatocyte liquid suspension (1–2 liters) separated from patient blood by a cellulose acetate dialysis membrane. Each treatment used fresh hepatocytes during a single four to six hour dialysis (run). Multiple runs successfully reduced serum bilirubin and reversed metabolic encephalopathy in a single case.

A controlled study from the USSR comparing dialysis against a hepatocyte suspension with standard medical therapy for support of acute liver failure was reported recently (Margulis et al. (1989) supra). The bioartificial device consisted of a small 20 ml cartridge filled with pig hepatocytes in liquid suspension, along with activated charcoal granules. The cartridge was perfused through a Scribner arteriovenous shunt access. Patients were treated daily for six hours. The hepatocyte suspension was changed hourly over each six hour treatment period. Improved survival was demonstrated in the treated group (63%) when compared with the standard medical therapy control group (41%).

Culturing hepatocytes with a hollow fiber cartridge is another example of bioartificial liver support. Traditionally, hepatocytes are loaded in the extracapillary space of the hollow fiber cartridge, while medium, blood or plasma is perfused through the lumen of the hollow fibers. Cells may be free in suspension (Wolf & Munkelt "Bilirubin conjugation by an artificial liver composed of cultured cells and synthetic capillaries" *Trans ASAIO* (1975) 21:16–27); attached to walls (Hager et al. "A Prototype For A Hybrid Artificial Liver" *Trans ASAIO* (1978) 24:250–253); or attached to microcarriers which significantly increase the surface area within the extracapillary space (Arnaout et al. (1990) supra).

Bilirubin uptake, conjugation and excretion by Reuber hepatoma cells within a hollow fiber cartridge was reported in 1975. (Wolf & Munkelt (1975) supra). Tumor cell suspensions were injected by syringe into the shell side of the compartment while bilirubin containing medium was perfused through the hollow fiber intraluminal space. That technique has not been reported clinically, possibly due to the risk of tumor seeding by hepatoma cells.

Another hollow fiber device developed for liver support uses hepatocytes attached to microcarriers loaded into the extracapillary cavity of a hollow fiber cartridge. In that device, blood flows through semi-permeable hollow fibers allowing the exchange of small molecules. Using that system, increased conjugated bilirubin levels have been measured in the bile of glucuronosyl transferase deficient (Gunn) rats. (Arnaout et al. "Development of Bioartificial Liver: Bilirubin Conjugation in Gunn Rats" *J Surg Research* (1990) 48:379–82) Since the outer shell is not perfused, all oxygen and nutrients are provided by the patient blood stream. In addition, that system may require an intact in vivo biliary tree for the excretion of biliary and toxic wastes.

However, for clinical applications, it is desirable to increase the liver-specific functions of the BAL, thereby requiring more cells or increasing the per cell liver-specific function. The former avenue generally is not considered because normal cells are difficult to obtain, the cells are difficult to maintain and the bioreactor cannot command a large blood volume during ex vivo therapy.

Primary rat hepatocytes, when plated on some modified surfaces, form aggregates that exhibit enhanced per cell liver-specific functions (Koide et al. "Continued High Albumin Production by Multicellular Spheroids of Adult Rat Hepatocytes Formed in the Presence of Liver-Derived Proteoglycans" *Biochem Biophys Res Commun* (1989) 161:385–391; Tong et al. "Long-Term Culture of Adult Rat Hepatocyte Spheroids" *Exp Cell Res* (1992) 200:326–332). Freshly isolated rat hepatocytes, when plated between 30–80% confluency onto positively charged polystyrene surfaces (Koide et al. "Formation of Multicellular Spheroids Composed of Adult Rat Hepatocytes in Dishes with Positively Charged Surfaces and Under Other Nonadherent Environments" *Exp Cell Res* (1990) 186:227–35), initially spread out and seem to move randomly. After 48 hours, cell movement appears directional as cells begin to aggregate into multicellular islands which eventually shed off into suspension as freely suspended aggregates. Aggregates formed in that manner exhibit a uniform diameter of approximately 100 µm and are 6–8 cell layers thick.

Reported systems for making aggregates include culture of aggregates in a polyurethane foam matrix in a packed bed culture system (Ijima et al. "Application of Three Dimensional Culture of Adult Rat Hepatocytes in PUF Pores for Artificial Liver Support System" *In: Animal Cell Technology: Basic & Applied Aspects* Murakami et al. Ed., (1992) pp 81–86, Kluwer Academic Publishers, The Hague, Netherlands), culture of aggregates in a tubular reactor packed with pyrex glass beads (Li et al. "Culturing of Primary Hepatocytes as Entrapped Aggregates in a Packed Bed Bioreactor: A Potential Bioartificial Liver" *In Vitro Cell Dev Biol* (1993) 29A:249–254), culture of calcium alginate-encapsulated aggregates in a spouted bed culture chamber (Takabatake et al. "Encapsulated Multicellular Spheroids of Rat Hepatocytes Produce Albumin and Urea in a Spouted Bed Circulating Culture System" *Artif Organs* (1991) 15:474–480; Koide et al. "Hepatocyte Spheroid: Differentiated Features and Potential Utilization for Bioreactor of Artificial Liver Support" Extended Abstract, Japanese Association of Animal Cell Technology Annual Meeting, Nov. 9–12, 1993, Nagoya, Japan) and collagen-entrapped aggregates inoculated into the extracapillary space of a hollow fiber bioreactor (Sakai and Suzuki "A Hollow Fiber Type Bioartificial Liver Using Hepatocyte Spheroids Entrapped in Collagen Gel" Extended Abstract, Japanese Association of Animal Cell Technology Annual Meeting, 1993, Nagoya, Japan).

A common limitation of each of those systems is the low number of hepatocytes attainable for use in the bioreactor. Approximately 50 million through 75 million hepatocytes as aggregates were used in those studies. The aggregate formation process using stationary petri dishes or other surfaces is long and labor intensive. Aggregate formation occurs only within a narrow cell density range (approximately $3-8 \times 10^4$ cells/cm$^2$). Of the cells initially plated, only 30–40% of the inoculated cells form aggregates after 2–3 days of culture. Thus, to supply 100 million hepatocytes as aggregates, an inoculum of approximately 300–400 million cells is required. Based on plating density requirements, that translates to a surface area of 8000 cm$^2$ or 200 petri dishes of 60 mm diameter. Thus, the feasibility of employing reconstituted hepatocytes (aggregates) in a bioartificial liver application depends on the ability to engineer reconstituted hepatocyte formation at a quicker rate and a higher efficiency.

The availability of a higher number of aggregates would enable maximization of viable cells in the BAL without detrimentally increasing the size of the device.

SUMMARY OF INVENTION

An object of the instant invention is to provide an artificial liver comprising hepatocytes formed into organoids to maximize per cell liver-specific functions. A combination of preformed organoids and dispersed hepatocytes are entrapped within a contracted matrix gel in a hollow fiber to allow perfusion by a luminal nutrient flow stream.

BRIEF DESCRIPTION OF DRAWINGS

FIG. 2A relates to monolayer cultures and FIG. 2B relates to collagen-entrapped cells. The plots denoted by circles in both panels relate to organoids and the plots denoted by squares in both panels relate to single cells.

DETAILED DESCRIPTION OF THE INVENTION

Figure 1:
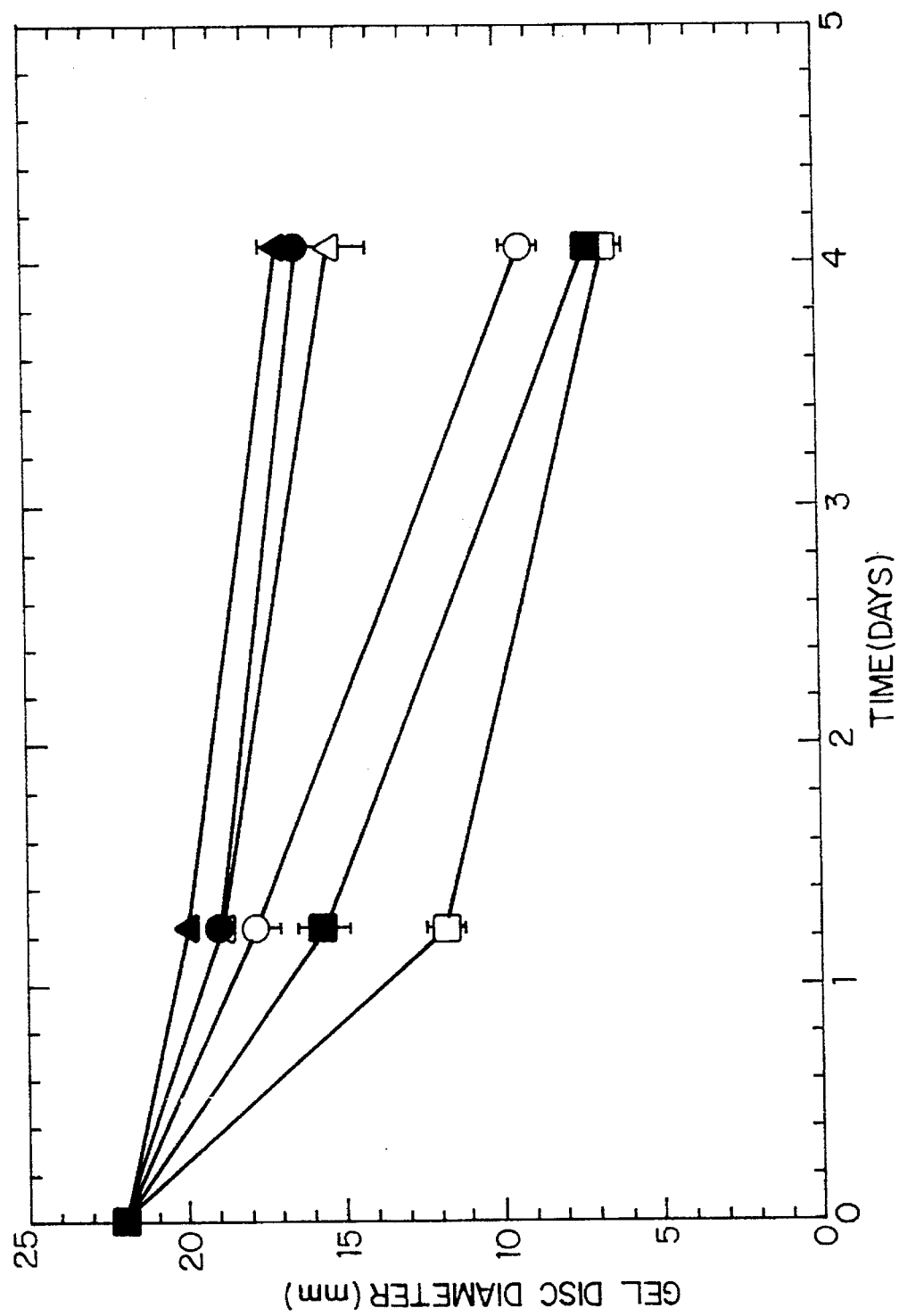
FIG. 1 depicts the degree of gel compaction when cells, organoids or a combination thereof are entrapped within. In the graph, the curve denoted with open squares represents $5 \times 10^6$/ml dispersed cells; the filled squares represent $1 \times 10^6$/ml dispersed cells; the open circles, $2.5 \times 10^6$/ml cells in organoids and $2.5 \times 10^6$/ml dispersed cells; the filled circles, $0.5 \times 10^6$/ml each of cells in organoids and dispersed cells; the open triangles $5 \times 10^6$/ml cells in organoids; and filled triangles $1 \times 10^6$/ml cells in organoids.

A bioreactor device suitable for the instant invention is set forth in copending application, U.S. Ser. No. 08/376,095 filed 20 Jan. 1995, herein incorporated by reference in entirety. A bioreactor according to the inventive principles of the instant invention generally would include two chambers within a housing means having a proximal end and distal end.

The two chambers are generated by a porous membrane. In one chamber are the hepatocytes and in the other chamber would flow the blood, plasma or serum. In a preferred embodiment, the membrane is in the form or porous-walled hollow fibers with the hepatocytes contained in the lumen of the fibers.

The preferred membrane selectively allows low and high molecular weight compounds, such as nutrients and cell products, to cross between the chamber containing the cells and the other chamber. The desired upper molecular weight limit of the membrane is variable and can be varied to suit a specific purpose. Thus, a suitable membrane for a BAL may be on the order of 100,000 to allow free passage of most sub-cellular molecules. Ultrafiltration membranes that could be used with a bioreactor system of the instant invention include those made from polysulfone, nylon, polypropylene, polyester/polycarbonate, ionically charged membranes, cellophane®, nitrocellulose, polyethylene and ceramics. A few commercial examples include polycarbonate and polyester Nucleopore® membrane filters from Nucleopore Corporation in Pleasanton, Calif.; polysulfone PTGC membranes from Millipore of Bedford, Mass.; and nitrocellulose Collodion® membranes from Schleicher and Schuell, Inc. in Keene, N.H.

For the purposes of modifying a reactor to serve as a BAL, it is preferable to employ a hollow fiber bioreactor. A suitable hollow fiber assembly is the Amicon PN 5407 Model DH4 from Amicon, a division of W. R. Grace & Co. in Danvers, Mass., with the pressure control valve and filter frits removed. In that case the hollow fibers are constructed of the various porous membrane materials with the inner compartment of the fibers serving as the site where the organoids and cells are housed. An Amicon H1P3-100 hollow fiber membrane assembly having an upper molecular weight limit of approximately 100,000 can be used. The hollow fibers of that assembly are formed of polysulfone, although any suitable membrane composition as discussed above also may be employed successfully.

Because a principle function of the instant device is to detoxify blood, plasma or serum, the pore size must be selected to enable passage of most known toxins into the hollow fibers. It is known that many toxins and metabolites are conjugated or attached to carrier molecules in the circulation. A common carrier molecule is albumin. For example, it is known that unconjugated bilirubin is carried by albumin. Thus, it is beneficial to have pores which would enable passage of molecules about the size of albumin, which has a molecular weight of about 70,000 through the walls of the fiber.

The hollow fibers can be obtained commercially in a variety of lengths and diameters. Suitably, the fiber lengths are conformed to the size of the housing. Fiber diameter is selected to maximize the number of cells contained therein, to maximize the flow of nutrient medium to retain maximal cell viability, to maximize surface area within the fiber and on the outer surface of the fiber and to retain an adequate size to house organoids.

Fibers having a diameter of up to about 1 mm are used routinely and a diameter of about 100 µm probably represents a practical lower limit for the size of the fibers. Fibers of more intermediate diameter can be used and it often is preferred to use fibers having a diameter of about 150–400 µm so as to maximize the number of fibers that can be maintained in the housing. Thus, fibers of about 200–250 µm also are suitable.

A suitable hollow-fiber assembly has a housing having spaced end portions defining a chamber therebetween. The housing has a first and second fluid inlet means with the second fluid inlet means positioned generally toward the inside of first fluid inlet means. The housing also has a first and second fluid outlet means, with the second fluid outlet means positioned generally toward the inside of the first fluid outlet means. While the housing is generally cylindrical, shape is not so limited. Any housing which will house hollow fibers may be employed successfully.

Within the housing is at least one selectively permeable hollow fiber, pervious to the passage of nutrients and cell products while substantially impervious to the passage of cells, extending the length of the housing. The hollow fiber divides the chamber into an intracapillary space within the hollow fiber and an extracapillary space outside the hollow fiber. The intracapillary space and extracapillary space communicate only through the walls of the hollow fiber. Preferably, the intracapillary space provides a cell chamber for cells entrapped in the chosen matrix and a secondary lumen for passage of nutrient medium while the extracapillary space provides space for the blood, plasma or serum to bathe the outer surface of the fibers. The roles may be reversed, if desired. Preferably, a plurality of fibers would be employed. The interior lumens of the hollow fibers are in flow communication with the first fluid inlet means and the first fluid outlet means. The extracapillary space is in flow communication with the second fluid inlet means and second fluid outlet means.

A bioreactor apparatus using the principles of the instant invention provides high oxygen transfer to the entrapped cells to maintain cell viability within the bioreactor with a low shear flow. The results further demonstrate that rapid start-up of the bioreactor apparatus is possible as well as step changes from serum-containing medium to serum-free medium and in many cases even protein-free medium. A "step change" means to change instantaneously rather than gradually.

Generally, the cell-biocompatible matrix or gel is formed when the chosen cells are mixed with a matrix precursor solution at lower temperatures (e.g., 0° C. to 30° C.), at lower pH values (e.g., 2 to 5.5), at both a lower temperature and a lower pH value, or in a solution of different ionic makeup. The chosen matrix precursor is preferably initially in a soluble form to create the cell suspension. The cell-matrix precursor suspension then is introduced into the cell chamber through an inlet means. When the pH, the temperature or ionic character or polymer chain interaction is changed from the initial value, polymerization or aggregation occurs with the resulting polymer chains forming insoluble aggregates (e.g., pH value increased to the range of 6.8 to 7.4, temperature increased to the range of 37° C. to 45° C.). Generally, the insoluble aggregates will aggregate further to form fibers. The fibers, in turn, entrap the cells creating what is referred to as the substantially insoluble, cell-biocompatible matrix.

It is desired that the chosen matrix precursor have the ability to form rapidly a substantially insoluble, biocompatible matrix in situ to entrap uniformly the cells, before the cells settle. The chosen matrix precursor preferably should form the fibrous matrix on a physical or chemical change in the cell-matrix precursor suspension. Such a change could be the result of a shift in pH or temperature value, or both, addition of a comonomer or any other initiator of polymerization or cross-linking, or any combination of those methods. Depending on the chosen matrix precursor, the formed matrix could be the result of polymerization, aggregation, ionic complexation, hydrogen bonding or the like.

For the sake of convenience, it should be understood that wherever the term polymer or aggregate is used to refer to the matrix construction, the matrix is not limited to compounds with those characteristics. Any biocompatible, substantially insoluble matrix that forms in situ and entraps cells, at least initially, is considered to be within the scope of the present invention. Likewise, the matrix precursor should be read to include, but not be limited to, all compounds which tend to polymerize or aggregate or associate or the like to form the matrix in situ.

Due to contraction possibly caused by the living cells contained therewithin, the cell-biocompatible matrix will contract, sometimes to about one quarter of the original volume occupied by the mixture in a few hours or days. For the instant invention it is necessary for the cell-biocompatible matrix to contract within the fiber to provide a lumen therewithin for the passage of nutrients. A cell-matrix which contracts to approximately 90% of the original volume occupied by the mixture is desired. A cell-matrix which has contracted to approximately 75% of the original volume occupied is even better. A cell-matrix which has contracted to approximately 50% of the original volume is preferred even more. However, the most desirable cell-matrix will contract to approximately one-third of the original volume occupied by the mixture.

One compound that has been found to form a particularly suitable matrix is collagen. Sterile, high purity native ateleopeptide collagen Type I is commercially available from Collagen Corporation in Palo Alto, Calif. under the trade name Vitrogen™ 100. Teleopeptide collagen Type I also has proven to be useful and is available in a relatively pure form from Gottefosse Corporation located in Elmsford, N.Y. under the trade name Pancogene S™. Whenever the term collagen is used in the instant application, it should be read to include any type of collagen or modified collagen which is at least partially insoluble under optimum cell culture conditions. For example, collagen may be modified according to the techniques of U.S. Pat. No. 4,559,304 to Kasai, et al., the disclosure of which is incorporated by reference herein.

The collagen-cell solution is introduced into the fibers to set in situ by increasing the ambient temperature to greater than about 25° C., preferably about 35°–45° C., and ideally about 37°–43° C.

A collagen-chitosan mixture also may be used. A suitable chitosan, which is a derivative of chitin in which many of the N-acetyl linkages have been hydrolysed to leave the free amine, can be obtained from Protan Labs of Redmond, Washington in a dry state under the label Ultrapure Chitosan. As in the case of collagen, it should be recognized that the chitosan also can be modified chemically and still be an effective means for forming the matrix. In addition, the in situ polymerization of a fibrinogen and thrombin mixture to form fibrin has been employed successfully.

Other materials which would meet the requirements of this system include: (1) polyamines wherein the subunits which make up the polymer have a $pK_a$ value generally ranging from 7 to 10, such as collagen and chitosan. Such polyamines are soluble in a cell culture media at pH values generally in the range of 2 to 5.5 when in a protonated form and partially insoluble in a cell culture media at pH values generally ranging from 6.8 to 7.4 when in a partially unprotonated form; (2) a mixture of water soluble polyanionic polymers and polycationic polymers. This mixture would associate through ionic bonds and fall out of solution; and (3) polymers, such as cellulose ethers, which are soluble in a cell culture media temperatures ranging from 0° C. to 30° C. but insoluble in a cell culture media at higher temperatures, such as those generally ranging from 32° C. to 45° C. have also been contemplated.

In operation, the chosen cell nutrient medium is pumped with a peristaltic pump, from a media reservoir through the first fluid inlet means and first medium channel(s) to the nutrient medium plate window(s). A suitable pump is a variable speed Masterflex Cat. No. 7533-30 with size 16 Masterflex silicone tubing from Cole Palmer in Chicago, Ill. Medium continues through the nutrient medium plate window(s) to the second medium channel(s) and subsequently out bioreactor through the first fluid outlet means.

Hepatocytes can be obtained by any of a variety of art-recognized means. Gentle treatment of the organ and cells is recommended to enhance viability. For example, perfusion with a solution containing a digestive enzyme, such as collagenase, is a suitable method. The animal is anethesized and the hepatic vasculature isolated. The liver is perfused with a buffer, preferably a calcium-free buffer containing a divalent cation chelator to enhance replacement of blood in the organ and to begin dissolution of the intercellular matrix.

The liver is excised and then perfused with a buffer containing collagenase. The capsule is compromised and the organ manipulated to release the cells. The cells are washed and viability assessed by standard methods, such as trypan blue exclusion.

Organoids are obtained by taking the hepatocyte single cell suspension in a hormonally-defined serum-free medium containing insulin, dexamethasone, glucagon, epidermal growth factor, liver growth factor, transferrin, linoleic acid, copper, selenium and zinc. The cells are placed in a siliconized spinner flask and stirred at about 40–120 rpm and preferably about 70–90 rpm and more preferredly at 80 rpm in a humidified 5% $CO_2$ environment. The medium can be changed after 24 hours and every 2–3 days thereafter.

Generally, the dynamics of organoid formation are uniform across the species origin of the cells. However, it is notable that the time frame within which organoids form can vary from species to species. Usually, cells first amass in clumps of two's, three's, four's and the like. Then over time, the clumps become larger as either clumps coalesce or individual cells adhere to the larger clumps. Thus, at an early time point, organoids may be on the order of about 20–30 μm in diameter, at a next time point, the organoids may have increased in size to about 35–40 μm in diameter, to about 100–140 μm on a successive reading and so on. Organoids of about 150–300 μm in diameter are observed routinely.

With respect to preferred sizes of organoids to be incorporated into the hollow fibers, it is noted that maximal viability may be ensured with smaller sized organoids, however it is desired that a maximal number of cells be contained in the bioreactor. Moreover, it is desired that the cells retain liver-specific functions and the size of the organoids may play a role in the retention of those desirable activities.

The organoids, or hepatocyte cell masses, to be incorporated into the hollow fibers can range in size from about 30–300 μm in diameter. Certain occasions may command that the idealized size of the cell masses be on the order of about 35–150 μm in diameter to a more narrow range of about 40–70 μm in diameter.

Preferably the hepatocytes are entrapped in an aqueous, porous gel, such as alginate, collagen, agar, chitosan, fibrin and the like. A mixture of organoids and single cells are mixed together to attain the necessary contraction of the formed gel in the hollow fibers to form a "secondary lumen" or the "occluded lumen" of the fiber to enable passage of the nutrient medium.

The ratio of organoids to single cells is optimized to assure adequate gel contraction with the maximal number of entrapped cells. A ratio of cells in organoids to single cells of 1:3 to 3:1 can be used. A preferred ratio of 1:2 to 2:1 is preferred. A ratio of 1:1 also can be used beneficially.

The matrix-cell solution is infused into the fibers via the ports described hereinabove. The sizes of the organoids and the total number of cells to be contained in the fiber lumen are adjusted by manipulating the cell number in the matrix solution prior to gelation. The number of cells in organoids is assessed and that number is added to the number of single cells to obtain a total cell number.

As indicated hereinabove, a goal is to obtain the maximal number of cells in the bioreactor to ensure efficient detoxification of the blood, serum or plasma. A suitable concentration of total number cells is on the order of about $5$–$40\times10^6$ cells per milliliter. A more suitable concentration is about 20–40 million cells per ml and an ideal concentration is about 30–35 million cells per ml. It should be made clear that from that idealized cell number, the number of cells found in organoids then is calculated based on the desired ratios of cells in organoids to single cells discussed hereinabove. Hence, when using a cell concentration of $30\times10^6$ cells/ml and a 1:1 ratio of organoids to single cells, $15\times10^6$ cells will be in organoids and the other half of the cells are single cells.

By using the cell masses, organoids of the instant invention, which are produced at an accelerated rate by the method disclosed herein, it is possible to maximize and retain liver-specific function. By doing so, an enhanced bioreactor is obtained because the device per se can be reduced in size, that is the housing can be reduced in size, so as to minimize the need to have a large extracorporeal blood volume in the device.

The instant invention is exemplified in the following non-limiting examples.

EXAMPLE I

Porcine Organoids Formed in a Stirred Vessel Exhibit Enhanced Liver Activities

Porcine hepatocyte harvest

Hepatocytes were harvested from 8–10 kg male pigs by a two-step in situ collagenase perfusion technique modified from the original method developed for rat hepatocytes by Seglen (Seglen, P. O. "Preparation of Isolated Rat Liver Cells" *Meth Cell Biol* (1976) 13:29–38). The porcine first was anesthetized with ketamine (100 mg/ml): rompun (100 mg/ml), 5 ml:1 ml, IM to allow for intubation and mechanical ventilation. The porcine then was anesthetized with isofluorane (1.5%) per endotracheal tube and paralyzed with succinylcholine (20 mg IV). The abdomen was entered through a bilateral subcostal chevron incision.

The venous vascular supply to and from the liver was isolated completely and looped with ties. The hepatic artery, common bile duct, gastrohepatic omentum and phrenic veins were ligated. The portal vein was cannulated with pump tubing and perfusion was initiated at 300 ml/min with oxygenated perfusion solution I (Per I). Per I is a calcium-free solution with 143 mM sodium chloride, 6.7 mM potassium chloride, 10 mM hydroxyethylpiperazine-ethane-sulfonic acid (HEPES)(Gibco, Grand Island, N.Y.) and 1 g/l ethylene glycol-bis-aminoethyl ether (EGTA), at pH 7.40. The suprahepatic and infrahepatic vena cavae were ligated and a vent was made in the infrahepatic cava to modulate perfusion back pressure.

The liver was excised, placed in a large sterile basin and perfused at 300 ml/min with oxygenated perfusion solution II (Per II). Per II consisted of 100 mM HEPES, 67 mM sodium chloride, 6.7 mM potassium chloride, 4.8 mM calcium chloride, 1% (v/v) bovine albumin and 1 g/l collagenase-D (Boehringer-Mannheim, Indianapolis, Ind.), pH 7.6. After 20–30 min, on visual and palpable evidence of the liver dissolving, the capsule was broken and the liver substance was raked and irrigated with cold Williams' E medium (Gibco) supplemented with 15 mM HEPES, 0.2 U/ml insulin (Lilly), 2 mM L-glutamine, 100 U/ml penicillin and 100 μg/ml streptomycin. The released cells were filtered through nylon mesh with 100 μm openings and resuspended in fresh Williams' E medium. Viability was assessed by trypan blue exclusion.

Formation of pig hepatocyte organoids in a stirred vessel

Isolated pig hepatocytes were resuspended in hormonally-defined culture medium, referred to as LTE medium, at a concentration of $0.5$–$1\times10^6$ cells/ml. The medium was a modification of the serum-free medium of Enat et al. (Enat et al. "Hepatocyte Proliferation In Vitro: Its Dependence on the Use of Serum-Free Hormonally Defined Medium and Substrata of Extracellular Matrix" *Proc Natl Acad Sci USA* (1984) 81:1411–1415) containing Williams' E basal medium supplemented with 100 units/ml penicillin, 100 μg/ml streptomycin, 0.2 units/ml insulin (Lilly Co., Indianapolis, Ind.), 1 nmole/ml dexamethasone, 4 ng/ml glucagon, 25 μg/ml EGF, 20 ng/ml liver growth factor, 6.25 μg/ml transferrin, 50 ng/ml linoleic acid, 500 µg/ml albumin, 0.1 µM $CuSO_4 \cdot 5H_2O$, 3 nM $H_2SeO_3$, 50 pM $ZnSO_4 \cdot 7H_2O$ and 15 mM HEPES (Gibco) at pH 7.4. All the medium supplements were from Sigma unless otherwise specified. The cell suspension was placed into 250 ml siliconized spinner flasks and stirred at 80 rpm by a suspended magnetic stir bar in a humidified 5% $CO_2$ incubator at 37° C. Medium was changed 24 hr after cell inoculation and every 2–3 days thereafter by stopping agitation, allowing gravity sedimentation of the organoids, followed by aspiration of the spent medium and replacement with fresh medium.

Hepatocytes cultured in stirred conditions form organoids within 24 hr. During the formation period, cells first agglomerated to form multicellular aggregates of irregular shape and "bumpy" boundaries; individual cells still were discernible. Subsequent rearrangement and compaction of cell aggregates gave rise to structures with relatively smooth, undulating outer surfaces and individual cells at that time were indistinguishable from each other.

By 24 hr, almost all aggregated cells were in the form of organoids. The diameter of organoids was assessed under an inverted microscope using a 10× ocular lens equipped with a vernier scale. Only particles above 30 µm in diameter were counted. The average of lengths along two perpendicular axes of the organoid was defined as the organoid diameter. Between 80–100 were evaluated to obtain representative average diameters. Organoids grew in size from 40–70 µm in diameter on the first day to 100–140 µm after five days in culture.

For comparison, monolayer cultures also were performed. Freshly isolated hepatocyte suspensions ($5 \times 10^5$ cells/ml) in LTE medium were used to inoculate 12-well tissue culture polystyrene plates (Falcon Multiwell, Becton Dickinson, Franklin Lakes, N.J.) at 2 ml/well. Culture medium was replaced daily with fresh medium, while the spent medium was collected and stored frozen at $-20°$ C. until assayed. No organoids were formed during the observation period, although organoids will form on prolonged culture.

Ultrastructure of organoid formed under stirred conditions resemble those formed on surfaces Scanning electron microscopy of organoids at five days in culture showed that most were relatively spherical except for some dumbbell-shaped, ones probably formed by coalescence of two organoids. At a higher magnification extensive cell-cell contact, numerous microvilli and small (2–4 µm) holes on the surface of the organoid can be seen. Such holes frequently were found at contact points of three cells. One might speculate that those pores on the organoid surface are localized in areas of junction between adjacent cells and are surface openings of differentiated bile canaliculus-like structures.

Transmission electron microscopy of hepatocytes in organoids exhibited extensive cell-cell contact and nuclei of round or oval shape. Numerous mitochondria and lipid droplets of various sizes were observed in the cytoplasm of several cells. Morphologic characteristics predominant in organoids are junctional complexes, such as desmosomes, and bile canaliculus-like structures between hepatocytes. Continuous ductular structures of approximately 0.1 µm in diameter were distributed throughout the organoid 15 and can be seen to open as pores on the organoid surface.

Numerous microvilli protruded into the structures. Organoids formed under stirred conditions appear structurally identical to those formed in petri dishes.

Liver-specific functions of organoids formed under stirred conditions
Ureagenesis Urea production by hepatocytes cultivated as monolayers and as organoids was compared using known techniques. The number of hepatocytes inoculated per unit volume of medium was the same in both cases. After measuring urea concentration for each time point, the daily production of urea was calculated. The rate of urea production divided by the initial hepatocyte concentration was taken as the specific urea production rate.

Specific productivity in both cultures increased for the first three days and then gradually decreased. Hepatocytes cultured as free organoids were two times more active in urea production than cells grown as monolayers on tissue culture plates.

Albumin production

Albumin synthesis by organoids in spinner flasks and cells cultivated as monolayers was measured using known techniques, such as by ELISA or RIA, and expressed as cumulative values over seven days. Specific albumin synthesis rates were determined by a linear regression fit of the data.

The albumin production rate for organoid and monolayer cultures were determined to be 50 µg/$10^6$ cells/day and 14 µg/$10^6$ cells/day, respectively. Organoids were at least three times more active than monolayers in producing albumin.

Lidocaine metabolism

The cytochrome P-450 function of hepatocyte organoids entrapped in collagen was evaluated by monitoring lidocaine metabolism using known techniques. Disappearance of exogenously added lidocaine alone was not a sufficient representation of P-450 activity, as the drug might be taken up by the hepatocytes without further biotransformation. Thus, production of lidocaine metabolites, e.g. monoethylglycinexylidide (MEGX), in addition to lidocaine clearance, were measured, using known techniques, to validate the quantification of P-450.

Lidocaine clearance remained relatively constant at about 28 µg/$10^6$ cells/day over a 21-day period. MEGX-specific production also was maintained relatively constant at a rate of approximately 1.2 µg/$10^6$ cells/day, demonstrating the continuous function of the cytochrome P-450 enzyme system. 4-Methylumbelliferone (4-MU) conjugation The ability of hepatocyte organoids entrapped in collagen gel to conjugate was examined by assessing 4-MU metabolism using known techniques. 4-MU concentration decreased from 65 µM to below 0.1 µM within 24 hrs. The glucuronidated metabolite, 4-MUG, appeared in the culture medium. High glucuronidation activity was maintained in culture throughout the 21-day period. The sulfated 4-MU metabolite (4-MUS) could not be detected at a sensitivity of 1 µM. The activity represents the ability of pig hepatocyte organoids to carry out phase II metabolism for long time periods while entrapped in collagen gel.

EXAMPLE II

Rat Organoids Formed in a Stirred Vessel Exhibit Enhanced Liver Activities

Rat hepatocyte harvest

Hepatocytes were harvested from 4–6 week old male Sprague-Dawley rats by a modified two-step in situ collagenase perfusion technique (Seglen, P.O. (1976) supra; Nyberg et al. "Primary Culture of Rat Hepatocytes Entrapped in Cylindrical Collagen Gels: An In Vitro System With Application to the Bioartificial Liver" *Cytotechnology* (1992) 10:205–215). Post harvest hepatocyte viability ranged from 85–90% based on trypan blue exclusion.

Formation of rat hepatocytes organoids in a stirred vessel

Freshly harvested dispersed rat hepatocytes were inoculated into 250 ml siliconized spinner vessels to a final density of $0.3$–$1.0 \times 10^6$ cells/ml in 100 ml LTE medium, identical to that used for formation of pig hepatocyte organoids in spinner vessels. The medium is different from that used for rat hepatocyte organoid formation in petri dishes. The vessels were stirred with a suspended magnetic stir bar at 100 rpm in a humidified 5% $CO_2$ incubator at 37° C. Medium was exchanged every 3–4 days by halting agitation to allow gravity sedimentation of organoids, followed by aspiration of spent medium and replacement with fresh medium.

Rat hepatocytes cultured in stirred conditions formed organoids within 72 hrs after inoculation. During the first 8 hr period, cells were observed to form mostly doublets and triplets. After 24 hrs, cells agglomerated into masses of over 30 cells. Subsequent rearrangement and compaction of cells gave rise to a population of spherical cell structures, or organoids, which displayed relatively uniform diameter of 100–140 µm and smooth outer surfaces.

To evaluate the efficiency of organoid formation, viability of cell suspensions during the formation period was determined. Single cells and cells in grouped masses that appeared blue under trypan blue exclusion were considered nonviable and unable to participate in organoid formation. It was assumed that only viable cells can form organoids.

At each sampling point, 2.5 ml cell suspensions were placed into 15 ml centrifuge tubes and separated by gravity sedimentation into two fractions. The cell aggregate fraction consisted mainly of organoids and cell aggregates that would settle within the first 2 minutes to the bottom of the 15 ml centrifuge tube. That fraction was resuspended in phosphate-buffered saline solution, sonicated and stored at −20° C. until the assay for total protein. The supernatant fraction contained the culture medium and most of the nonviable and unaggregated cells that had not settled within the first two minutes after sampling. All fractions were stored at −20° C. until liver-specific function assays were performed.

By 72 hrs, nearly all single cells in the spinner vessel were nonviable and all organoids appeared viable, based on fluorescence staining with ethidium bromide and fluorescein diacetate. Ethidium bromide stains nuclei of nonviable cells an orange-red and fluorescein diacetate stains cytoplasm of viable cells green. Determining the accumulation of nonviable cells and then performing a total cell balance around the vessel indicates that approximately 50–80% of inoculated cells formed into organoids. Consistently, the fraction of total protein in the organoid and aggregated cell fraction also was approximately 50–80% of the total protein content of the initial inoculum.

Ultrastructure of organoids formed under stirred conditions resemble those formed on surfaces Scanning electron microscopy indicates that organoids ranged in diameter of about 50–200 µm but the majority were of about a uniform size of about 120 µm in diameter and spherical in shape. Individual cells within the organoids were indistinguishable. At a higher magnification, extensive cell-cell contact, numerous microvilli and small pores apparently corresponding to bile canalicular-like structures, can be seen on the surface of the organoid. Transmission microscopy shows clear evidence of gap junctions between cells and an extensive network of microvilli-lined bile canalicular-like channels. The cytoarchitecture and ultrastructure of organoids appear to mimic that of an in vivo liver lobule. Electron microscopy indicates that organoids formed in a spinner flask to be structurally similar to organoids formed on flat surfaces.

Liver-specific functions of organoids formed under stirred conditions

Ureagenesis

After measuring urea concentrations, the daily production of urea by rat organoids in spinner cultures was calculated. The rate of urea production divided by the initial hepatocyte concentration was taken as the specific urea production rate.

Specific productivity decreased in the first 72 hrs, presumably due to 50% loss of viability during organoid formation. After organoid formation, the specific rate held steady at approximately 24 µg/$10^6$ cells/day. By normalizing the production rate to total protein, specific productivity was approximately 120 µg/mg protein/day.

Albumin synthesis

Albumin concentrations in spinner flasks were measured and cumulative values were determined for seven days. Specific albumin synthesis rates were determined by linear regression fit of the data.

The albumin synthesis rate for organoids was 28 µg/$10^6$ cells/day. Specific synthesis rates of organoids formed on petri dishes were similar to that of organoids formed in spinner cultures.

EXAMPLE III

Collagen-entrapped Porcine Organoids From Stirred cultures

Collagen gel contraction

The observation of gel contraction is important to the application of organoids in the BAL system, since gel contraction is necessary for intraluminal perfusion of culture medium to the hepatocytes entrapped in a hollow fiber bioreactor. To study the rate of gel contraction, both organoids and dispersed hepatocytes were entrapped in disc-shaped collagen gels of 22 mm diameter and approximately 1.3 mm thickness.

Organoids were obtained from a 6 day spinner culture whereas the dispersed cells were used immediately after a separate hepatocyte harvest. The gel entrapment was performed by suspending cells in a collagen mixture consisting of 3:1 (v/v) mixture of Vitrogen 100 and four-fold concentrated Williams' E media adjusted to pH 7.4 and then plating the suspension into a 12 well-plate at 0.5 ml/well.

The six conditions studied were: (1) $1 \times 10^6$ cells as organoids per ml collagen mixture, (2) $1 \times 10^6$ dispersed cells per ml collagen mixture, (3) $0.5 \times 10^6$ cells as organoids and $0.5 \times 10^6$ dispersed cells per ml of collagen mixture, (4) $5 \times 10^6$ cells as organoids per ml collagen mixture, (5) $5 \times 10^6$ dispersed cells per ml collagen mixture, (6) $2.5 \times 10^6$ cells as organoids and $2.5 \times 10^6$ dispersed cells per ml of collagen mixture. As a control, hepatocytes were killed by exposure to 50% ethanol for 15 minutes before collagen entrapment. The number of cells as organoids was estimated based on total protein per ml in the 6-day spinner culture.

After incubating at 37° C. for 20 minutes the gel was formed. Subsequently, 1 ml of LTE medium was added to each well, and the gels were dislodged from the bottom of the plate to allow medium to reach the bottom of the gel. Gel diameter was measured with a ruler along two perpendicular axes for each gel. Each data point in FIG. 1 represents the average of triplicate measurements. The results demonstrate that viable hepatocytes are required for collagen gel contraction.

Both organoid and dispersed cells were able to contract collagen gel. However, the rate of gel contraction by dispersed hepatocytes is higher than that by hepatocytes entrapped as organoids. The rate of contraction by a combination of both single cells and organoids falls in between the rates of those entrapped separately. Contraction appears to be affected by cell concentration (Scholtz & Hu *Cytotechnology* (1990) 4:127–137; Nyberg et al. *Biotechnol Bioeng* (1993) 41:194–203) as the extent of contraction was higher in discs with a denser cell concentration. Contraction also is expected to be affected by the distribution of cells in the gel and may attribute to the difference in the contraction rate.

Liver-specific functions of collagen gel-entrapped organoids
Ureagenesis

Both dispersed cells and organoids were entrapped separately in collagen gel disks at the same cell concentration, submerged into medium and cultivated in 12-well plates.

Figure 2A:
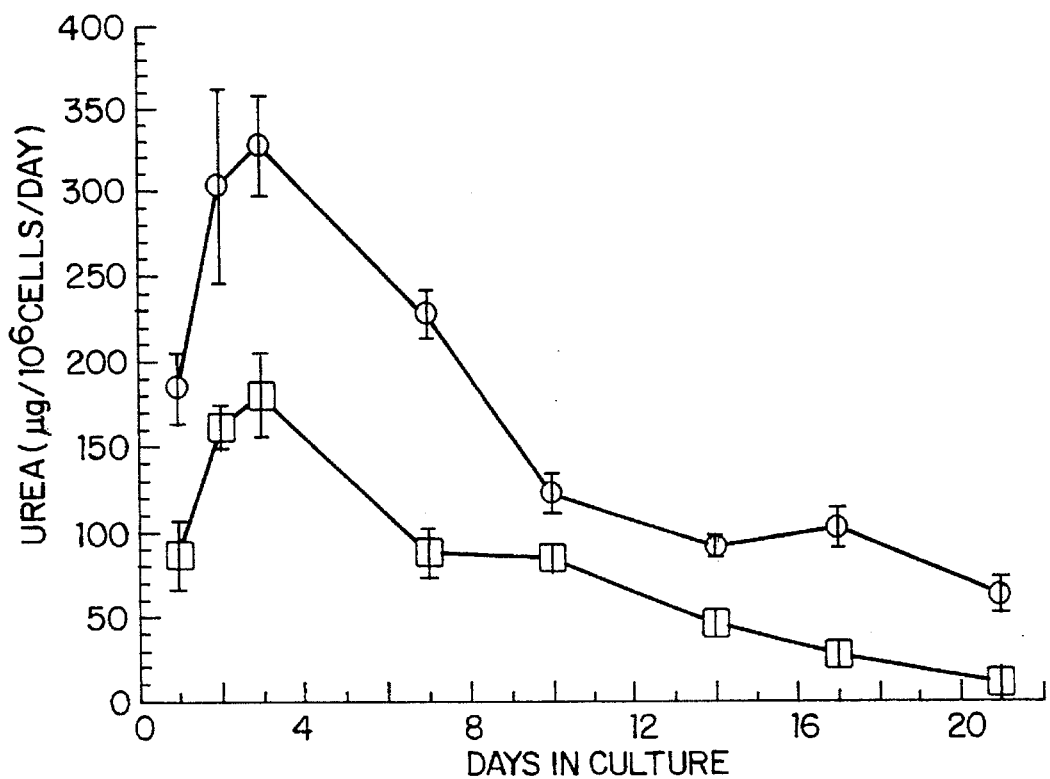
FIGS. 2A and 2B depict urea production by monolayer and collagen gel-entrapped cells and organoids.
Figure 2B:
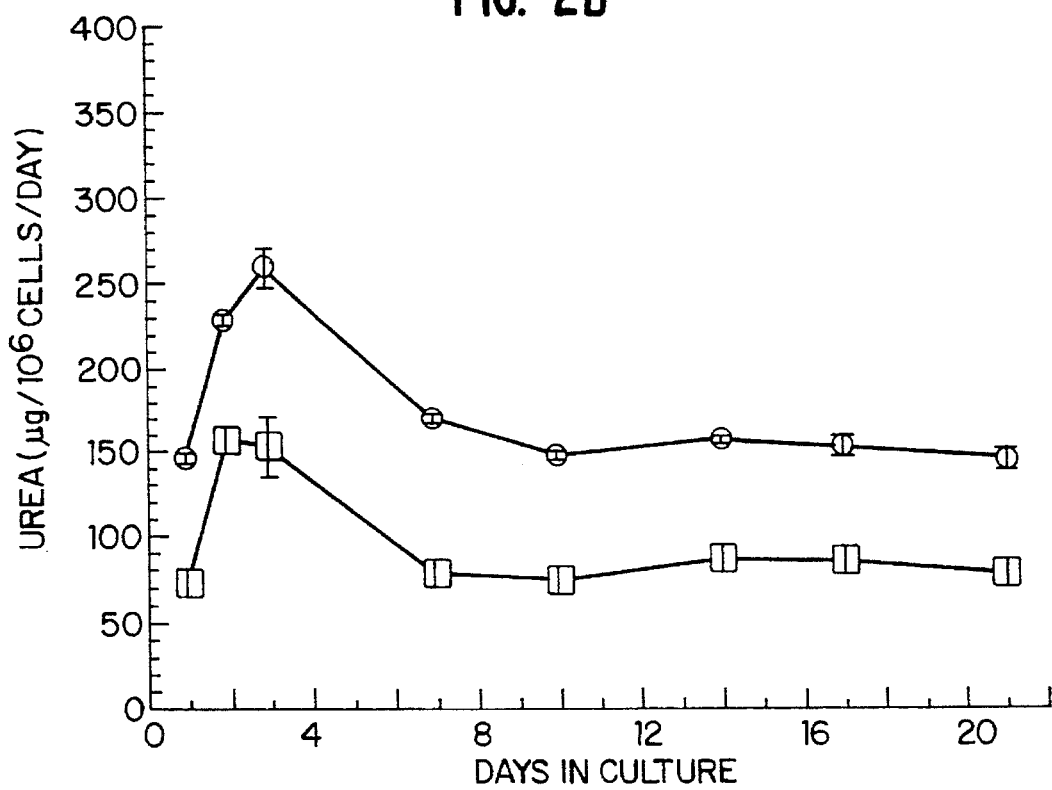

Comparison of the two culture systems indicate that urea production was higher in the organoid culture after collagen entrapment. Furthermore, urea production by both collagen-entrapped organoids and dispersed cells was more stable than those in free suspension or as a monolayer. After an initial increase in activity in the first three days, the urea production rate decreased to a level similar to the first day and remained relatively unchanged until day 21. Entrapment of organoids and unaggregated cells in collagen gels thus extended that activity (FIG. 2).

Albumin production

Figure 3:
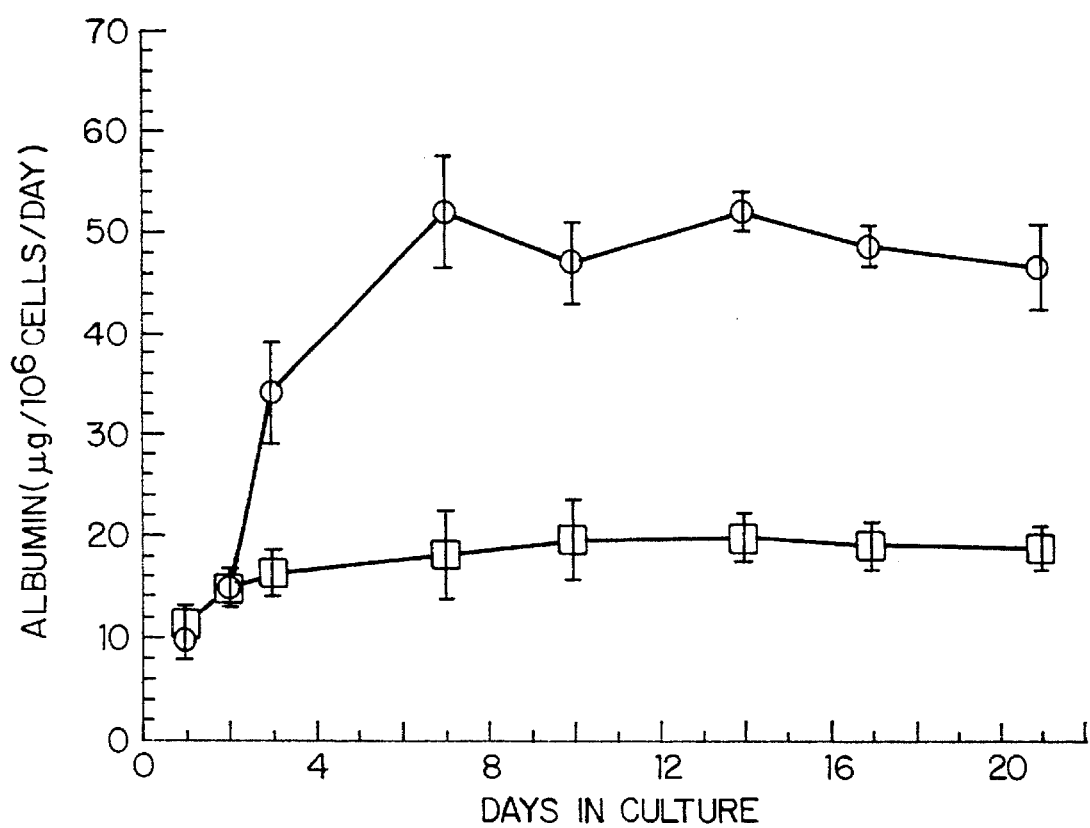
FIG. 3 depicts the levels of albumin production by collagen-entrapped organoids and dispersed cells. In the graph, circles relate to organoids and squares to single cells.

Albumin production by collagen-entrapped organoids and dispersed hepatocytes was measured for 21 days. The specific activities were calculated and are shown in FIG. 3.

After an initial period of increasing activity, the samples stabilized at approximately 50 µg/$10^6$ cells/day and 18 µg/$10^6$ cells/day, respectively. The levels were maintained for at least 21 days. The albumin synthetic activity of collagen-entrapped organoids was not significantly different from that in free-suspension or in monolayers. That production level is similar to the in vivo albumin production reported for human liver (Peters, P. "Proteins and Plasma Protein Metabolism" In *Molecular and Cell Biology of the Liver* 9 pp. 31–64 LeBouton, AV. (1993) Ed. CRC Press, USA).

EXAMPLE IV

Collagen-entrapped Rat Hepatocyte Organoids

Collagen Gel Contraction

Figure 4:
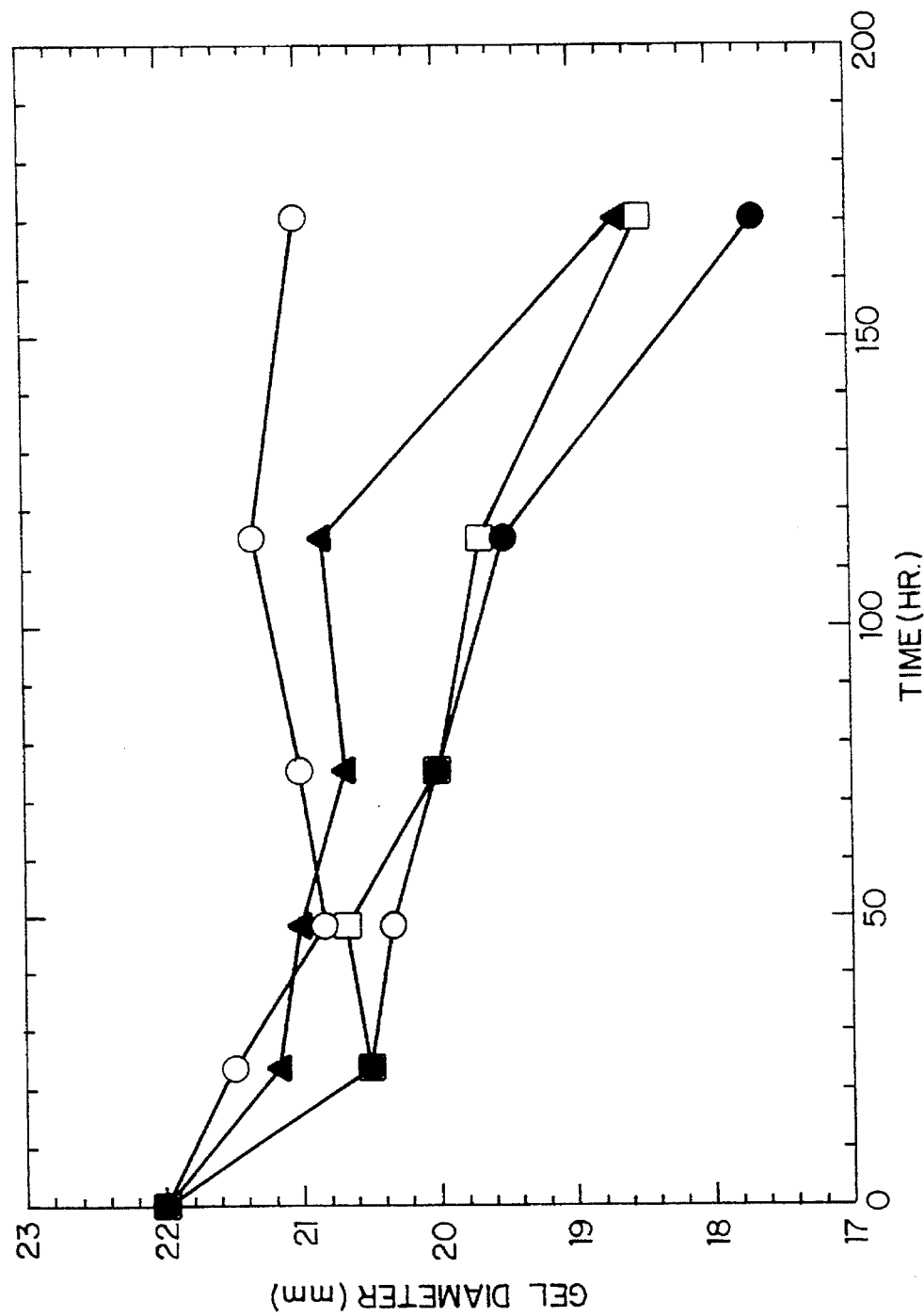
FIG. 4 depicts the level of gel contraction using organoids, cells and combinations thereof. The gel disc had a thickness of 1.3 mm. A million cells were incorporated into each disc. The open circles relate to organoids; the filled circles, dispersed cells; the triangles, a 2:1 ratio of cells in organoids to dispersed cells; and the squares, a 1:1 ratio of cells in organoids to dispersed cells.

Rat hepatocyte organoids from a 48 hr spinner culture and freshly harvested rat hepatocytes were mixed at various ratios and entrapped in collagen discs that were 22 mm in diameter and approximately 1.3 mm in thickness. The gel entrapment was performed by suspending cells in a 3:1 (v/v) mixture of Vitrogen 100 and four-fold concentrated Williams' E media adjusted to pH 7.4 and then plating the cell-collagen mixture into a 12-well plate at 0.5 ml/well. The four conditions studied were: (1) organoids at $10^6$ cells/ml without dispersed cells, (2) organoids and dispersed cells both at $10^6$ cells/ml, (3) organoids at $10^6$ cells/ml and dispersed cells at $0.5\times10^6$ cells/ml, (4) dispersed cells at $10^6$ cells/mi. After incubating at 37° C. for 20 minutes the gel was formed. Subsequently, 1 ml of LTE medium was added to each well and the gels were dislodged from the bottom of the plate to allow medium to reach the bottom of the gel. Gel diameter was measured with a ruler along two perpendicular axes for each gel. Each data point in FIG. 4 represents the average of triplicate measurements.

Without the addition of dispersed cells the gel containing organoid contracted only to a small degree. The presence of dispersed cells in the gel facilitated the contraction. The final diameter was about 30% smaller than at the beginning.

Liver-specific functions of collagen gel-entrapped organoids formed on petri dishes
Albumin synthesis Falcon Primaria culture dishes (60×15 mm) were plated with harvested freshly rat hepatocytes at $1.2\times10^6$ cells/plate and incubated in 5 ml organoid medium at 37° C. in a 5% $CO_2$ humidified incubator. The medium used for preparation of organoids on Primaria petri dishes consisted of Williams' E medium (Gibco Laboratories, Grand Island, N.Y.) supplemented with 0.2 U/ml bovine insulin (Lilly Research Laboratories, Indianapolis, Ind.), 2 mM L-glutamine, 15 mM N-2-hydroxyethylpiperazine-N'-2-ethane sulfonic acid (HEPES), 100 U/L penicillin and 100 mg/L streptomycin (Gibco Laboratories) with an additional 50 ng/ml epidermal growth factor (EGF), 50 ng/ml linoleic acid, 0.1 µM $CuSO_4.5H_2O$, 3 nM $H_2SeO_3$ and 50 pM $ZnSO_4.7H_2O$ (Sigma Chemical Company, St. Louis, Mo.). Organoid formation was observed by day 4.

The cellular contents of each petri dish, which contained a combination of unaggregated cells, clumped cells and organoids, were removed be gently pipetting. The contents of each plate were withdrawn into a 10 ml pipet and allowed to settle by gravity for 1 minute. The bottom one-fourth of each sample, consisting of mostly organoids and aggregated cells, was considered the organoid fraction. The top three-fourths, consisting of mostly unaggregated cells, was considered the dispersed cell fraction.

Based on total protein content, equal numbers of hepatocytes in the organoid fractions and the dispersed cell fraction were entrapped into cylindrical collagen gels and incubated in fresh organoid medium. An unseparated cell suspension, consisting of a mixture of both aggregated and unaggregated cells also was collagen-entrapped into cylindrical gels 4.5 days after plating.

Figure 5:
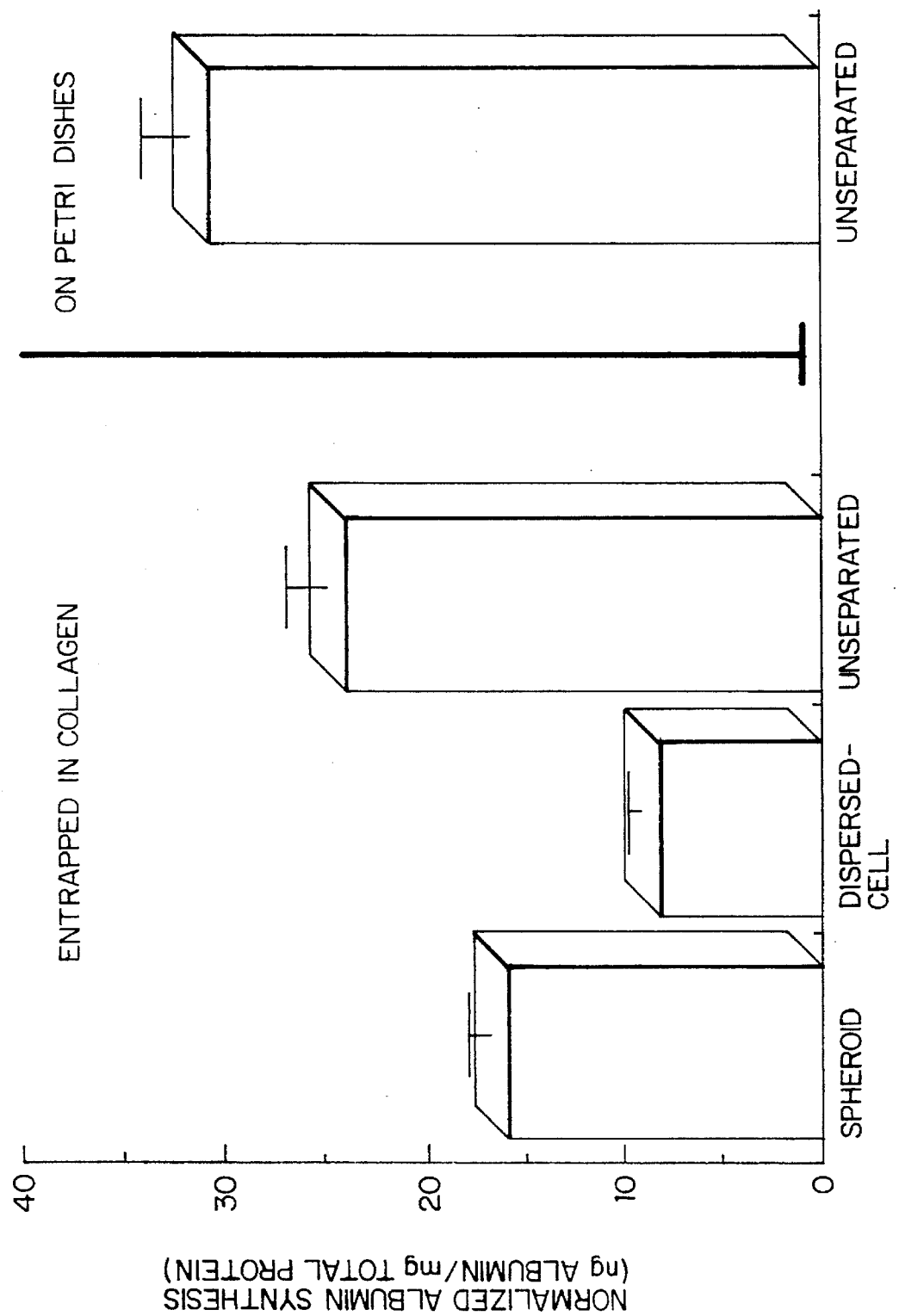
FIG. 5 depicts albumin production of collagen-entrapped aggregated and unaggregated cells.

Medium from the three different conditions were collected 7 days after plating, or 2.5 days after entrapment, and analyzed for albumin concentration. The results are shown in FIG. 5. The data were normalized to the total cellular protein present in each culture initially. Approximately two-fold higher activity of albumin synthesis was observed for the collagen-entrapped organoid culture as compared to the collagen-entrapped dispersed cell culture. The contributions from the two cell fractions approximately equaled the level of albumin produced by the unseparated cell mixture.

The three collagen-entrapment cultures were also compared to cells which had formed organoids and that had been maintained on Primaria dishes for the duration of the same experiment. In accordance with the collagen entrapment cultures, the dishes were refed with fresh organoid medium 4.5 days after modulation and albumin synthesis was measured on incubation to 7 days. Results indicate that even on entrapment in collagen gel, the unseparated cell entrapment culture was able to maintain a high level of albumin synthesis. The mixture of organoids and unaggregated cells which had been maintained in petri dishes showed comparable albumin synthesis levels.

Lidocaine metabolism

Lidocaine clearance rates were measured as an indicator of P-450 enzyme activity. Both organoid and dispersed-cell fractions from a 4.5 day petri dish culture were entrapped in cylindrical collagen gels at approximately equal amounts of total protein. Single cells entrapped into cylindrical collagen gels immediately after rat harvest also were included in the experiment as a control. The cylindrical gels were placed into wells holding 2 ml prewarmed organoid media containing 12 µg/ml lidocaine. In the subsequent five days, the spent medium was collected and replaced daily with fresh medium. The collected samples were analyzed for lidocaine clearance.

Figure 6:
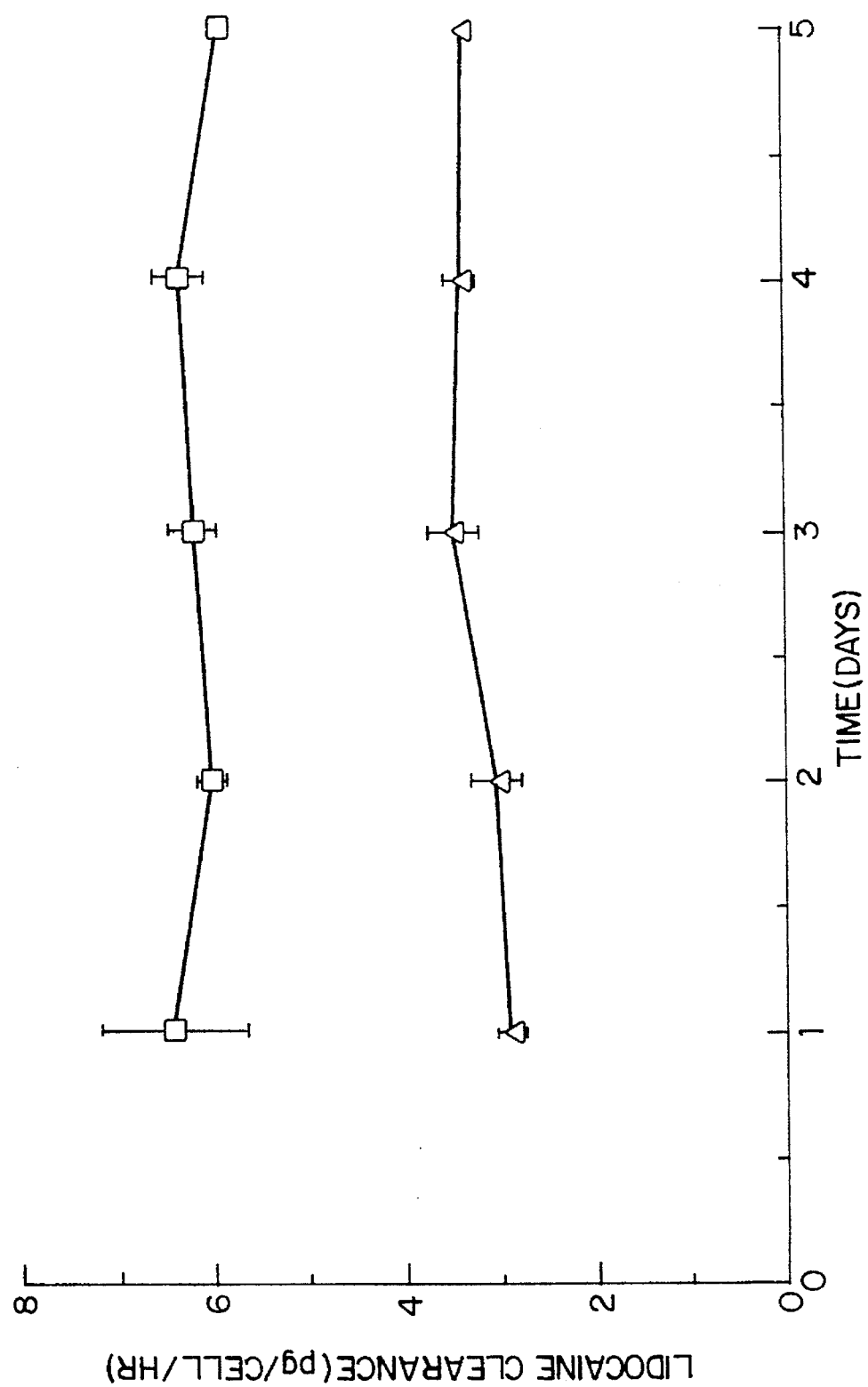
FIG. 6 depicts the lidocaine clearance rates of gel-entrapped cells and organoids. In the figure, the plot denoted by squares relates to organoids and that by triangles, dispersed cells.

By correlating cell number to total protein content, an average cellular protein content of 2.0 mg/cell was obtained and used to determine a specific lidocaine clearance rate. On entrapment into cylindrical collagen gels, the organoid and dispersed-cell fractions exhibited an average clearance rate of $6.2\pm0.5$ pg/cell/h and $3.2\pm0.4$ pg/cell/h, respectively (FIG. 6). The rate obtained in the organoid entrapped cylindrical collagen gels is approximately two-fold higher than the dispersed cell-entrapped cultures and more than three-fold higher than the rate of $1.7\pm0.2$ pg/cell by the control culture. The rate of the control culture is in good agreement with a previously reported specific clearance rate of $2.1\pm0.2$ pg/cell/h for static cultures of single cell hepatocytes entrapped in collagen.

Ultrastructure of entrapped organoids

Organoids were cultivated on Primaria dishes for 4.5 days and entrapped in collagen. The collagen-entrapped organoids were cultured for two days in organoid medium, then fixed and stained for microscopic observation. Scanning electron microscopy showed that individual cells within the organoid could not be distinguished. The overall structure of organoids remained intact after two days entrapment in collagen. When viewed under an inverted microscope, the collagen gels appeared contracted, presumably because unaggregated hepatocytes, which could not be completely separated from organoids prior to entrapment, are able to contract collagen fibers.

Similar to organoids in petri dishes, organoids entrapped in collagen appear to exhibit extensive cell-cell contact, abundant microvilli and small 2–4 µm openings on the surface of the entrapped organoids. The hole or pore structures, localized around cell junctions, may indicate differentiated and polarized cellular morphology of hepatocytes in organoids.

Transmission electron micrographs of collagen-entrapped organoids indicate an ultrastructure similar to that observed for organoids in petri dishes. Hepatocytes on the outermost layer are flattened, more epithelial in morphology and have a low cytoplasmic volume with large nuclei. The cells comprising the interior of the organoid are cuboidal and have smaller-sized nuclei with a larger cytoplasmic volume. Cell membranes and perinuclear structures remained intact; mitochondria with matricular bodies, peroxizomes, lipid droplets, glycogen granules, intact golgi apparatus and decorated rough endoplasmic reticulum were all visible. The extensive network of bile canaliculus-like structures between hepatocytes was maintained. The organization of hepatocytes within collagen-entrapped organoids was similar to that within suspended organoids. One striking difference between organoids in petri dishes and those entrapped in collagen is that the outermost hepatocytes of the latter are covered extensively by microvilli-like projections. In organoids maintained on petri dishes, surface microvilli on the outer layer of cells were less numerous and usually were localized to areas in and around the junction between adjacent hepatocytes.

EXAMPLE V

Bioartificial Liver (BAL)

A hollow fiber bioreactor can be used as a bioartificial liver by maintaining matrix-entrapped hepatocytes and hepatocyte organoids within the fibers, and perfusing a sustaining nutrient medium through the lumen along the space formed by matrix contraction, and passing blood around the fibers in the extracapillary space.

Thus, the stream of blood, serum or plasma to be detoxified flows through the shell side. Rather than residing in the extracapillary shell space, cells, such as hepatocytes, are within the hollow fiber lumen, entrapped in a gel matrix. That configuration is accomplished by first suspending hepatocytes in a solution of collagen or a mixture of collagen and extracellular matrix components. The pH then is adjusted to 7.4 and the cell suspension inoculated into the lumen of the hollow fiber. A temperature change from 4° C. to 37° C. induces collagen fiber formation. That results in cell entrapment in an insoluble fibrous and highly porous cylindrical gel.

After inoculation, the cross-sectional area of the gel-matrix cylinder can contract as much as 75%. That permits perfusion of the hollow fiber lumen even after it had been filled initially with the gel matrix. Molecular exchange occurs through the pores in the hollow fiber. Media with high molecular weight constituents flows through the hollow fiber containing a contracted core of hepatocytes embedded in a biomatrix through the hollow fiber inlet to the hollow fiber outlet.

The technique has been used with multiple cell lines including, Chinese hamster ovary cells, Hep2, HepG2, Vero, 293 cells and normal diploid human liver cells. Study of a hematoxylin and eosin (H & E) stained thin section of human hepatoblastoma (HepG2) cells within a contracted gel matrix after 7 days showed the tissue density and cytoarchitecture closely resemble in vivo histology.

The bioreactor offers distinct advantages over other configurations. Cells can be cultured at density close to that of tissue. At high density, cells occupy much less space, thus reducing the size of the bioreactor. Cells also obtain the benefits of close contact with minimal oxygen and nutrient limitations. Mammalian cells, at high density, may better preserve tissue specific function.

The bioreactor configuration also allows manipulation of the hepatocytes' local environment. Matrix constituents that support differentiated hepatocyte function can be incorporated into the gel. The ability to perfuse the inner lumen provides high molecular weight growth factors at high concentrations.

Another advantage of such a system is that different cell types can be co-entrapped in the gel to provide possible synergistic effects which may improve tissue specific function.

This invention is thus capable of incorporating many factors (medium, gel matrix, co-culture, high cell density) necessary or beneficial to sustain liver-specific functions. It can be used as a bioartificial liver to support patients in liver failure.

EXAMPLE VI

Collagen-entrapped Porcine Organoid BAL

A polysulfone hollow fiber cartridge (H1P3-100, Amicon, Danvers, Mass.) with a nominal molecular weight cut-off (MWCO) of 100 kiloDaltons (kD), an inner diameter of 1.1 mm and a total luminal volume of 10 ml was used as the BAL. The hollow fiber cartridge was autoclaved while immersed in distilled water for 30 minutes at 121° C. Other parts of the cultureware, including the oxygenator, media reservoir, pH probe and dissolved oxygen probe, were sterilized separately. The whole setup was assembled aseptically. The bioreactor was set up in a hollow fiber cell culture incubator, Acusyst Maximizer-1000 (Cellex Biosciences Inc., Coon Rapids, Minn.), which was microprocessor-controlled to maintain pH and dissolved oxygen by gas blending.

Freshly harvested primary pig hepatocytes were inoculated into spinner cultures at $1 \times 10^6$ cell/ml in LTE medium. After 24h, approximately 95% of cells had formed into organoids, while the remaining 5% remained suspended as single cells. Most of the single cells still were viable, as seen by ethidium bromide/fluorescein diacetate dual fluorescence viability staining. At the time, a total of 120 ml were removed from spinner vessels, aliquoted into 50 ml centrifuge tubes and centrifuged (34 g, 2 min) to a soft pellet. After aspirating the supernatant, the pellet then was resuspended into a pre-mixed collagen solution. The solution was prepared by mixing at 4° C. 15 ml Vitrogen, a type I collagen, and 5 ml four-fold concentrated Williams' E medium. The pH of the mixture was adjusted to 7.4 by drop-wise addition of sterile 1 N sodium hydroxide.

After suspending the organoid pellet the collagen solution, the cell-collagen mixture was injected slowly into the lumen space of the hollow fiber cartridge. A total of approximately 10 ml of solution was injected into the lumen space, or approximately $60 \times 10^6$ cells. Before inserting the cartridge into the cultureware, the entire cartridge was placed first in a 37° C. incubator for 10 minutes to allow the collagen mixture to gel. Approximately 400 ml prewarmed LTE media spiked with 4-methylumbelliferone (4-MU) were recirculated at 20 ml/min. Lumen perfusion at 9 ml/hr with medium alone was initiated after 24 hours. Medium from the intraluminal outflow was discarded after one pass. Every three days, medium from the extracapillary circuit was drained and replenished with fresh medium containing 12 µg/ml 4-MU. Samples were drawn from sterile septa on the extracapillary circuit and lumen outlets and stored at −20° C. until measurement of albumin, urea, 4-MU and metabolites was conducted. Lidocaine was added along with 4-MU, but due to adsorption of exogenous lidocaine to the cultureware, assessment of lidocaine clearance by cells could not be obtained readily.

Figure 7:
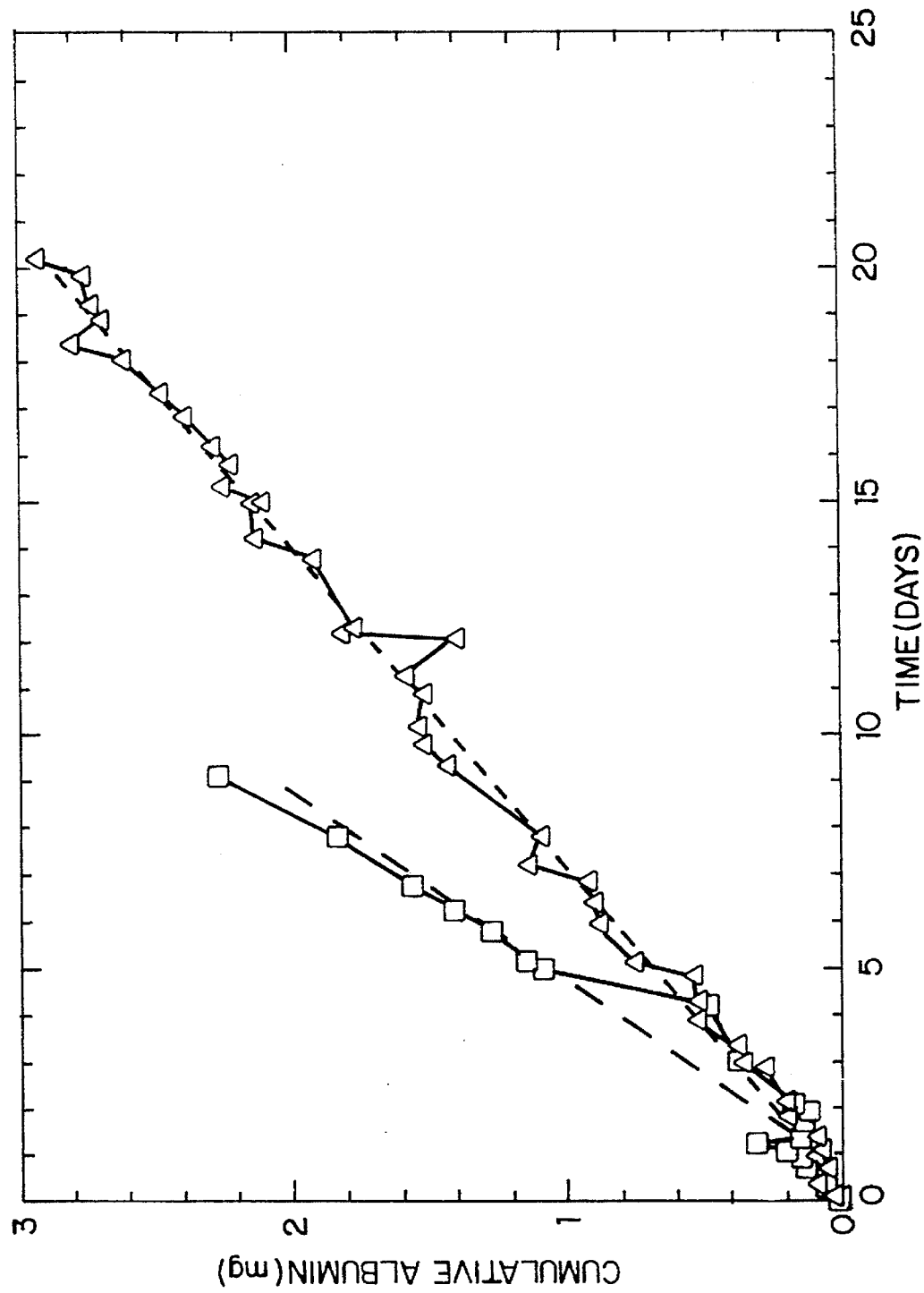
FIG. 7 depicts the albumin production rate of BAL's containing organoids or dispersed cells. The plot denoted by squares relates to organoids and that by triangles to dispersed cells.

Liver-specific functions higher in organoid-entrapped BAL than dispersed-cell BAL Albumin synthesis Albumin synthesis profiles were obtained for the extracapillary space and lumen outflow for both organoid-entrapped and dispersed-cell entrapped BAL's. A material balance taken around the hollow fiber bioreactor was performed to obtain a cumulative total rate of 0.25 mg/day for the organoid-entrapped BAL and 0.15 mg/day for the dispersed-cell BAL (FIG. 7). By dividing those values by the estimated number of hepatocytes in the BAL, as determined by total protein analysis, specific albumin synthesis rates of 0.2 pg/cell/hr and 0.1 pg/cell/hr, respectively, were obtained.

Ureagenesis

Figure 8:
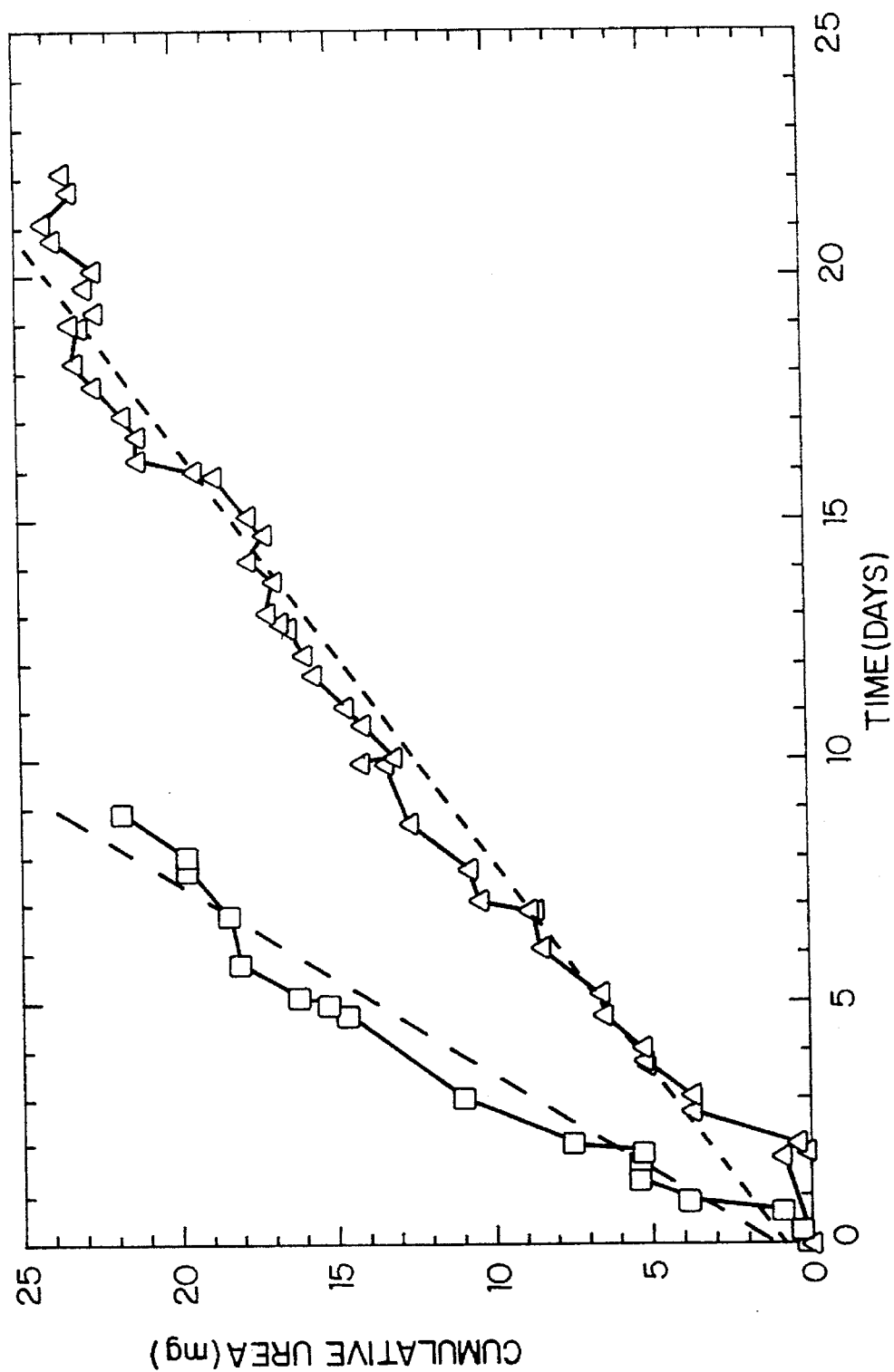
FIG. 8 depicts the urea generation rate for BAL's containing organoids or dispersed cells. The plot denoted by squares relates to organoids and that by triangles to dispersed cells.

Ureagenesis profiles were obtained for the extracapillary space and lumen outflow for both organoid-entrapped and dispersed-cell entrapped BAL's. A material balance taken around the hollow fiber bioreactor was performed to obtain a cumulative total rate of 2.57 mg/day for the organoid-entrapped BAL and 1.16 mg/day for the dispersed-cell BAL (FIG. 8). By dividing the values by the estimated number of hepatocytes in the BAL, as determined by total protein analysis, specific ureagenesis rates of 1.8 pg/cell/hr and 0.8 pg/cell/hr, respectively, were obtained.

4-MU metabolism

The ability of collagen-entrapped hepatocyte organoids in a BAL device to conjugate was examined by assessing 4-MU metabolism. Every three days, medium on the extracapillary circuit was drained and replenished with fresh LTE medium containing 35 µM 4-MU. Daily sampling indicated that concentrations of 4-MU decreased from 35 µM to below 1 µM within 24 hr. The glucuronidated metabolite, 4-MUG, appeared in the culture medium. High glucuronidation activity was maintained in culture for over 10 days. The sulfated 4-MU metabolite (4-MUS) could not be detected at an assay sensitivity of 1µM. The activity represents the capability of pig hepatocyte organoids to carry out phase II metabolism for long time periods in a BAL device.

EXAMPLE VII

Collagen-entrapped Rat Organoid BAL

A polysulfone hollow fiber cartridge (H1P3-100, Amicon, Danvers, Mass.) with a nominal molecular weight cut-off (MWCO) of 100 kiloDaltons (kD), an inner diameter of 1.1 mm and a total luminal volume of 10 ml was used as the BAL. The hollow fiber cartridge was autoclaved while immersed in distilled water for 30 minutes at 121° C. Other parts of the cultureware, including the oxygenator, media reservoir pH probe and dissolved oxygen probe were sterilized separately. The entire setup was assembled aseptically. The bioreactor was set up in a hollow fiber cell culture incubator, Acusyst Junior (Cellex Biosciences Inc., Coon Rapids, Minn.), which was microprocessor controlled to maintain pH and dissolved oxygen by gas blending.

Freshly isolated primary rat hepatocytes were plated onto 60×15 mm Falcon Primaria culture dishes (Becton Dickinson Laboratories, Oxnard, Calif.) at a density of 5.3 or $7.4 \times 10^4$ cells/cm$^2$ and incubated in 5 ml organoid medium. After 4 days, organoids and unaggregated hepatocytes were removed from the dishes by gentle pipetting. The mixture of organoids with unaggregated cells was centrifuged gently (34 g, 2 min), the supernatant was aspirated and the pellet was resuspended in a pre-mixed collagen solution. The solution was prepared by mixing at 4° C. 15 ml Vitrogen, a type I collagen, and 5 ml four-fold concentrated Williams' E medium. The pH of the mixture was adjusted to 7.4 by dropwise addition of sterile 1N sodium hydroxide. The collagen-cell mixture was inoculated into the luminal space of the hollow fiber cartridge. Approximately 500 ml prewarmed organoid media was recirculated at 200 ml/min on the extracapillary side to induce gelation of the collagen matrix. After gelation, or in approximately 30 minutes, the extracapillary medium recirculation rate was reduced to 35 ml/min. Within the first hour, the extracapillary medium was spiked with 12 µg/ml lidocaine by injecting lidocaine HCl (Abbott Laboratories, North Chicago, Ill.) into the extracapillary media reservoir. Lumen perfusion with organoid medium was initiated after 24 hours at 9 ml/hr. Medium from the intraluminal outflow was discarded after one pass. After 48 hours, medium on the extracapillary circuit was drained and replenished with fresh organoid medium containing 12 µg/ml lidocaine. Samples were drawn from sterile septa on the extracapillary circuit and lumen outlets and stored at −20° C. until measurement of albumin, lidocaine and its metabolites.

Two different cell concentrations were used in the inoculation of the bioreactor. For the low inoculation cell concentration, hepatocyte organoids were prepared from 54 Primaria culture dishes, each seeded with $1.5 \times 10^6$ cells suspended in 5.0 ml of organoid medium. For the high inoculation cell concentration, 152 Primaria dishes each were seeded with $2.1 \times 10^6$ cells. Medium was replaced after 2 days of culture. Organoids and unaggregated hepatocytes were removed from the dishes on day 4 by repeated gentle pipetting and suspended into enriched medium. The mixture of organoids and unaggregated hepatocytes was pelleted and resuspended in a collagen solution before inoculation into the bioreactor. The contents of one dish from each experiment were separated by gravity into a organoid fraction and a dispersed-cell fraction. Based on the total protein content of each fraction, 35% and 45% of the originally plated cells formed organoids for the low and high inoculation experiment, respectively.

Liver-specific functions higher in organoid-entrapped BAL than dispersed-cell BAL Oxygen uptake, albumin synthesis and lidocaine metabolism were used to evaluate organoid-entrapped BAL function. At the end of cultivation, fluorescence staining using fluorescein diacetate and ethidium bromide (Nikolai et al. "Improved Microscopic Observation of Mammalian Cells on Microcarriers by Fluorescent Staining" *Cytotechnology* (1991) 5:141–146) indicated good viability for hepatocytes in organoids. Most organoids were observed to maintain spherical morphology without disintegrating into single cells.

Oxygen uptake

A decrease in partial pressure of dissolved oxygen between the inlet and outlet of the bioreactor on the extracapillary space was observed, indicating oxygen consumption by the entrapped organoids and cells. The difference in partial pressure, multiplied by the solubility of oxygen in media at 37° C. ($1.29 \times 10^{-9}$ mol $O_2$ /ml/mm Hg) and by the extracapillary medium flow rate, yielded an average oxygen consumption rate of 24.5 μmoles $O_2$/h and 40.0 μmoles $O_2$/h for the low and high cell concentration bioreactors, respectively. Both reactors yielded similar specific oxygen uptake rates (OUR) of $0.6 \pm 0.3$ pmoles $O_2$/cell/h, after dividing the rates by the number of cells inoculated into each bioreactor, as determined by total protein analysis.

Albumin synthesis

Albumin synthesis profiles were obtained for the extracapillary space and lumen outflow for both studies. A material balance taken around the hollow fiber bioreactor was performed to obtain a cumulative total albumin synthesis rate of 13.0 μg/h and 80.6 μg/h for the low and high inoculation bioreactors, respectively. By dividing the values by the estimated number of hepatocytes in the BAL, as determined by total protein analysis, an average specific albumin synthesis rate of $0.54 \pm 0.04$ pg/cell/h was obtained.

Lidocaine Metabolism

Within the first hour after loading on the first day, the extracapillary medium of both bioreactors was spiked with 12 μg/ml lidocaine. On the third day, the o extracapillary medium was drained and replenished with fresh aggregate media containing 12 μg/ml lidocaine. Both lidocaine and MEGX were measured for the two reactors on day 1 and day 3 of culture.

In the bioreactor system the lidocaine added to the culture was adsorbed quickly onto the cultureware (bioreactor, tubing, oxygenator, medium reservoir). Thus lidocaine clearance was not a valid indication of metabolism. Instead the appearance of MEGX was used as an indicator of P-450 function. The specific production rate of MEGX was $0.11 \pm 0.04$ pg/cell/h (Table 1).

Previously, using a bioreactor entrapped with single cells, a comparable specific MEGX production rate of $0.08 \pm 0.04$ pg/cell/h was reported (Shatford et al. "Hepatocyte Function in a Hollow Fiber Bioreactor: A Potential Bioartificial Liver *J. Surg. Res.* (1992) 53:549–557).

Table 1 summarizes the metabolic activities of the BAL containing entrapped organoids versus with single-cell hepatocytes. The specific albumin synthesis rate for the organoid entrapped BAL was observed to be higher as compared to the single cell-entrapped BAL. The P-450 activity in the organoid-entrapped BAL also was higher, although to a lesser extent.

The results indicate that enhanced specific, or per cell, liver functions for hepatocytes cultivated as organoids are maintained on collagen-entrapment. When entrapped in collagen gel for two days, organoids were observed to retain overall morphology. Ultrastructural evaluation suggests that organoids possess the ability to detect the presence of extracellular matrix proteins, as indicated by the presence of microvilli on the outermost surface of the organoid. Supplementing the entrapment matrix with Matrigel, laminin being the major constituent, led to improved maintenance of albumin synthesis as compared to collagen-entrapped organoids.

TABLE 1

SUMMARY OF COMPARISON OF DISPERSED-CELL-ENTRAPPED AND ORGANOID-ENTRAPPED BAL FUNCTION

| CRITERION | SINGLE-CELL-BAL | ORGANOID-BAL |
| --- | --- | --- |
| Oxygen uptake rate (pmoles $O_2$/cell/hour) | $0.4 \pm 0.3$ | $0.6 \pm 0.3$ |
| Albumin synthesis rate (pg/cell/hour) | $0.12 \pm 0.01$ | $0.54 \pm 0.04$ |
| MEGX production rate (pg/cell/hour) | $0.08 \pm 0.04$*  $0.05 \pm 0.04$ | $0.11 \pm 0.04$ |

*based on previously reported data (Shatford et al. (1992) supra)

All references cited herein are incorporated by reference in entirety.

It will be evident that various modifications and changes can be made to the teachings set forth herein without departing from the spirit and scope of the instant invention.

We claim:

1. A filter device comprising:

a housing having first inlet and outlet ports defining a fluid flow cavity therebetween for flowing through said housing blood, serum or plasma;

said cavity also enclosing a plurality of hollow fibers having porous walls and a partially occluded lumen;

said porous walls comprising pores smaller than a hepatocyte;

said lumen of said hollow fibers are in fluid flow communication with second inlet and outlet ports in said housing for flowing through said lumen a medium to support hepatocyte function and viability; and said lumen of said hollow fibers are partially occluded with an aqueous matrix comprising viable hepatocytes, wherein said hepatocytes are a mixture of unaggregated cells and aggregated cell masses;

such that communication between said cavity and inside said hollow fibers is exclusively though the porous fiber walls.

2. The device of claim 1, wherein said hollow fibers have an inside diameter of 100–1000 μm.

3. The device of claim 2, wherein said inside diameter is 150–400 μm.

4. The device of claim 3, wherein said inside diameter is 200–250 μm.

5. The device of claim 1, wherein said pores allow passage of molecules with a molecular weight of up to 100,000.

6. The device of claim 1, wherein said medium is a serum-free medium.

7. The device of claim 1, wherein said matrix is selected from the group consisting of collagen, alginate, chitosan and fibrin.

8. The device of claim 7, wherein said matrix is collagen.

9. The device of claim 1, wherein said cell masses are 30–300 μm in diameter.

10. The device of claim 9, wherein said cell masses are 35–150 μm in diameter.

11. The device of claim 10, wherein the cell masses are 40–70 μm in diameter.

12. The device of claim 1, wherein said aqueous matrix is introduced into said fiber as a liquid and allowed to gel in situ, wherein said matrix gel contracts in the presence of said viable hepatocytes.

13. The device of claim 12, wherein said liquid contains hepatocytes at a concentration of $5$–$40 \times 10^6$ cells per milliliter.

14. The device of claim 13, wherein said concentration is $20$–$40 \times 10^6$ cells per milliliter.

15. The device of claim 14, wherein said concentration is $30$–$35 \times 10^6$ cells per milliliter.

16. The device of claim 13 wherein a half of the cells are in cell masses.

17. The device of claim 13 wherein two-thirds of the cells are in cell masses.

18. The device of claim 1, wherein said lumen is occluded 25–90% by said matrix.

19. The device of claim 18, wherein said lumen is occluded 33–75%.

20. The device of claim 1, wherein said hepatocytes are porcine hepatocytes.

* * * * *